US008623620B2

(12) United States Patent
Ju et al.

(10) Patent No.: US 8,623,620 B2
(45) Date of Patent: Jan. 7, 2014

(54) MICROORGANISM WHICH PRODUCES L-AMINO ACID AND METHOD FOR PRODUCING L-AMINO ACID USING THE SAME

(75) Inventors: Jae Yeong Ju, Seongnam-si (KR); Kwang Ho Lee, Daejeon (KR); Hyun Ae Bae, Seoul (KR)

(73) Assignee: CJ Chieljedang Corporation, Seoul (KR)

( * ) Notice: Subject to any disclaimer, the term of this patent is extended or adjusted under 35 U.S.C. 154(b) by 0 days.

(21) Appl. No.: 13/254,072

(22) PCT Filed: Feb. 16, 2010

(86) PCT No.: PCT/KR2010/000932
§ 371 (c)(1),
(2), (4) Date: Nov. 7, 2011

(87) PCT Pub. No.: WO2010/101359
PCT Pub. Date: Sep. 10, 2010

(65) Prior Publication Data
US 2012/0122163 A1    May 17, 2012

(30) Foreign Application Priority Data
Mar. 3, 2009 (KR) .................. 10-2009-0018127

(51) Int. Cl.
*C12N 9/24* (2006.01)
(52) U.S. Cl.
USPC ....................................... 435/115; 435/252.3
(58) Field of Classification Search
USPC .............................................. 435/115, 252.3
See application file for complete search history.

(56) References Cited

U.S. PATENT DOCUMENTS

| | | | |
|---|---|---|---|
| 6,610,836 B1 * | 8/2003 | Breton et al. | 536/23.1 |
| 7,179,623 B2 * | 2/2007 | Livshits et al. | 435/106 |
| 7,229,794 B2 * | 6/2007 | Park et al. | 435/71.2 |
| 2006/0019355 A1 | 1/2006 | Ueda et al. | |
| 2009/0246835 A1 | 10/2009 | Iwatani et al. | |

FOREIGN PATENT DOCUMENTS

| KR | 10-2006-0084446 A | 7/2006 |
|---|---|---|
| KR | 10-2008-0059604 A | 6/2008 |

OTHER PUBLICATIONS

Devos et al., Proteins: Structure, Function and Genetics. Practical Limits of Function Prediction. vol. 41: 98-107, 2000.*
Whisstock et al., Quarterly Reviews of Biophysics 2003, Prediction of protein function from sequence and structure. vol. 36 (3): 307-340, 2003.*
Witkowski et al.,Biochemistry. Conversion of a â-Ketoacyl Synthase to a Malonyl Decarboxylase by Replacement of the Active-Site Cysteine with Glutamine. 38:11643-11650, 1999.*
Seffernick et al., J. Bacteriol. Melamine Deaminase and Atrazine Chlorohydrolase: 98 percent identical but functionally different. 183(8): 2405-2410, 2001.*
Broun et al., Science. Catalytic Plasticity of Fatty Acid Modification Enzymes Underlying Chemical Diversity of Plant Lipids. 282:1315-1317, 1998.*
Lee et al., Mol. Sys. Biol. Systems metabolic engineering of *Escherichia coli* for L-threonine production. 3:149, 2007, 8 pages.*
Reid et al., Appl. Microbiol. Biotechnol. Sucrose utilization in bacteria: genetic organization and regulation 67: 312-321, 2005.*
McClelland et al., *Klebsiella pneumoniae* subsp. pneumoniae MGH 78578, complete sequence. Accession #CP000647—embedded in Office Action, 2007.*
Hiratsuka, K., et al., "Regulation of Sucrose-6-Phosphate Hydrolase Activity in *Streptococcus mutans*: Characterization of the *scrR* Gene," *Infect. Immun.* 66(8):3736-3743, American Society for Microbiology, United States (1998).
Jahreis, K. and Lengeler, J.W., "Molecular analysis of two ScrR repressors and of a ScrR-FruR hybrid repressor for sucrose and D-fructose specific regulons from enteric bacteria," *Mol. Microbiol.* 9(1):195-209, Blackwell Scientific Publications, England (1993).
Reid, S.J., and Abratt, V.R., "Sucrose utilisation in bacteria: genetic organisation and regulation," *Appl. Microbiol Biotechnol.* 67:312-21, Springer-Verlag, Germany (2005).
Sauter, T. and Gilles, E.D., "Modeling and experimental validation of the signal transduction via the *Escherichia coli* sucrose phosphor transferase system," *J. Biotechnol.* 110:181-199, Elsevier Science Publisher, Netherlands (2004).
Wang, J., et al., "Moldeling of inducer exclusion and catabolite repression based on a PTS-dependent sucrose and non-PTS-dependent glycerol transport systems in *Escherichia coli* K-12 and its experimental verification," *J. Biotechnol.* 92:133-158, Elsevier Science Publishers, Netherlands (2001).
International Search Report (ISR) for PCT/KR2010/000932, I.A. filed: Feb. 16, 2011, mailed Oct. 13, 2010 from the Korean Intellectual Property Office, Daejeon, Republic of Korea.
International Preliminary Report on Patentability and Written Opinion of the International Searching Authority for International application No. PCT/KR2010/000932, The International Burau of WIPO, Geneva, Switzerland, issued on Oct. 25, 2011.

* cited by examiner

*Primary Examiner* — Tekchand Saidha
*Assistant Examiner* — Rama P Ramanujam
(74) *Attorney, Agent, or Firm* — Sterne, Kessler, Goldstein & Fox P.L.L.C.

(57) ABSTRACT

The present invention relates to a microorganism belonging to the genus *Escherichia* sp. and a method for producing L-amino acid using the same. The microorganism belonging to the genus *Escherichia* sp. has a sucrose assimilability and L-amino acid producing ability, which is obtained by introducing a gene encoding a sucrose assimilative microorganism-derived sucrose metabolic enzyme to sucrose non-assimilative microorganism belonging to the genus *Escherichia* sp. having an L-amino acid producing ability and sucrose PTS (phosphoenolpyruvate dependent sucrose phosphotransferase system) activity.

12 Claims, 1 Drawing Sheet

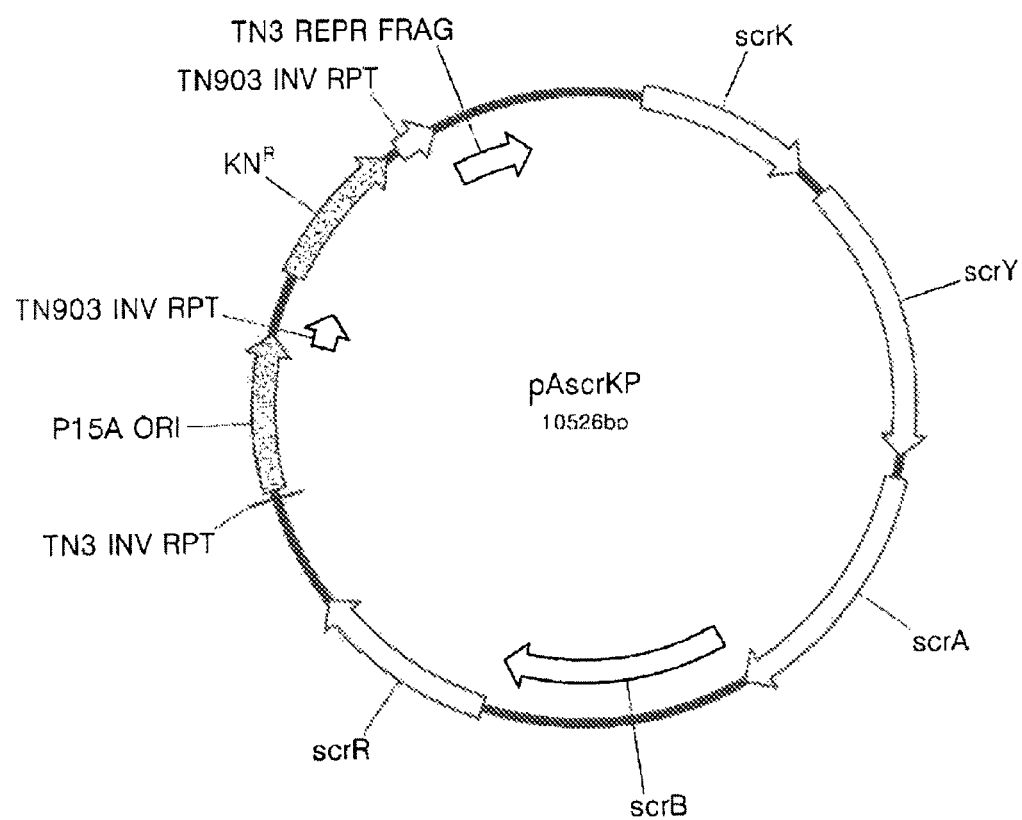

```
                        SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: Primer for amplification of scrKYABR from
      Klebsiella pneumoniae

<400> SEQUENCE: 1
cctcgtgcac agatgcgtag tcagcgtcag                                      30

<210> SEQ ID NO 2
<211> LENGTH: 36
<212> TYPE: DNA
<213> ORGANISM: Artificial Sequence
<220> FEATURE:
<223> OTHER INFORMATION: Primer for amplification of scrKYABR from
      Klebsiella pneumoniae

<400> SEQUENCE: 2
aaccaggcct actagtggat gttaagccgg gcgctg                               36

<210> SEQ ID NO 3
<211> LENGTH: 31
<212> TYPE: DNA
<213> ORGANISM: Artificial Sequence
<220> FEATURE:
<223> OTHER INFORMATION: Primer for amplification of scrKYABR from
      Erwinia carotovora

<400> SEQUENCE: 3
gccagtgcac ccctgaccgt aatagtgaag g                                    31
```

```
<210> SEQ ID NO 4
<211> LENGTH: 36
<212> TYPE: DNA
<213> ORGANISM: Artificial Sequence
<220> FEATURE:
<223> OTHER INFORMATION: Primer for amplification of scrKYABR from
      Erwinia carotovora

<400> SEQUENCE: 4
gccgaggcct actagtcagg cagataaaag cgtcga                                 36

<210> SEQ ID NO 5
<211> LENGTH: 7038
<212> TYPE: DNA
<213> ORGANISM: Klebsiella pneumoniae(ATCC700721)

<400> SEQUENCE: 5
gtgcacagat gcgtagtcag cgtcagcttc tggtaccgat cgtaaatatc gccaaaactg       60
gggttcatcg cgctacgcac tcctttacct ttggccaccg cggcgggct aaccgcgacc       120 tggtgaacta tacctaagcg ggtggggaag gaaaagtcca gatctggagt ggcgaaatat      180
tccgcctggc tcacattttt taccctcgcc tccctgtttc gtgacccaat cgttccgctt      240
accggtgggc tgtgctttaa tgagctaaac cggtttaata agtttagct tagaggagct       300 tgtcgtatga atggaaaaat ctgggtactc ggcgatgcgg tcgtcgatct cctgcccgat      360
ggagagggcc gcctgctgca atgccccggc ggcgcgccgg ccaacgtggc ggtcggcgtg      420
gcgcggctcg gcggtgacag cgggtttatc ggccgcgtcg gcgacgatcc cttcggccgt      480
tttatgcgtc acaccctggc gcaggagcaa gtggatgtgg actatatgcg cctcgatgcg      540
gcgcagcgca cctccacggt ggtggtcgat ctcgatagcc acggggagcg cacctttacc      600
tttatggtcc gtccgagcgc cgacctgttc cttcagcccg aggatctccc gccgtttgcc      660
gccggtcagt ggctgcacgt ctgctccatc gctctcagcg cggagccgag ccgcagcacg      720
acattcgcgg cgatggaggc gataaagcgc gccggggct atgtcagctt cgaccccaat       780
atccgcagcg acctgtggca ggatccgcag gaccttcgcg actgtctcga ccgggcgctg      840
gccctcgccg acgccataaa actttcggaa gaggagctgg cgtttatcag cggcagcgac      900
gacatcgtca gcggcaccgc ccggctgaac gcccgcttcc agccgacgct actgctggtg      960
acccagggta agcgggggt ccaggccgcc ctgcgcgggc aggttagcca cttccctgcc     1020
cgcccggtgg tggccgtcga taccaccggc gccggcgatg cctttgtcgc cgggctactc     1080
gccggcctcg ccgcccacgg tatcccggac aacctcgcag ccctggctcc cgacctcgcg     1140
ctggcgcaaa cctgcggcgc cctgccacc accgccaaag cgccatgac cgccctgccc       1200 tacagggacg atcttcagcg ctcgctgtga tcccttggg ccggttaacg cccactttg       1260 ctggcgacat cacaattctt aaaccggttt agcaattttt attttcaccg cgttaccgac     1320
atgtttacca tatcaactaa accggtttag caaacgttag cacactcact gatttacctt     1380
tggatgtcac caacatgtat aaaaaacgga agttagccat tcttattgct ttgctaaccg     1440
gcaccgccgc cgcccatggg cagacagacc tgaacagcat tgaagcgcgt ctcgccgccc     1500
tggaaaaacg cctgcaggac gccgagaccc gcgccagcac tgccgaaagc gcgccgcct     1560 cagcggagca gaaagttcag cagttaaccc agcagcagca gcaaacccag gccaccaccc     1620
agcaggtggc caggcgcacc actcaactgg aagaaaaagc cgaacggccc ggcggctttg     1680
agttccacgg ctatgcgcgt tccggggtga tcatgaacga ctcggccgcc agtaccaaat     1740
ccggcgctta tgaccccc gccggggaga ccggcggcgc cattggtcgc ctgggcaacc       1800
```

```
aggccgacac ctatgtggaa atgaacctcg aacataaaca gaccctggac aacggggcga   1860
ccacccgttt caaagtgatg gtggccgacg gacagaccac ttataacgac tggacggcaa   1920
gcagcagcga tctgaacgtg cgccaggcgt tcgtcgagct gggcaacctg ccgaccttcg   1980
aaggcccgtt cagaggctcg accctgtggg ccgggaaacg ctttgaccgc gacaacttcg   2040
acatccactg gattgactcg gatgtggtgt tcctcgccgg gaccggcggc gggatctacg   2100
acgtgaaatg gaacgacagc ctgcgcagca acttctcgtt atacggccgc aactttggcg   2160
atatcgccga cagcagcaac agcgtgcaga actatatcgt cagcatgaat aactttgccg   2220
gcccggtgcg gatgatggtc agcgggatgc gggcgaaaga taatgacgac cgccaggacg   2280
cgaacggcaa tctggtgaaa ggcgatgccg ctaacaccgg ggttcatgcc ctgctgggcc   2340
tgcacaatga gagcttctat ggcctgcgcg acgggaccag caaaacggcc ctgctgtacg   2400
gccacgggct gggcgccgag gttaaaggca tcggctccga cggcgcgctg cgcccggggg   2460
ccaatacctg gcgcttcgcc agctatggca ccacgccgct gagcgatcgc tggtttattg   2520
ccccggccgt gctggcgcag agcagtaaag atcgttatgt cgatggcgac agctatcagt   2580
gggccaccct caacctgcgt ctgattcagg aagtgacgca gaacttcgcc ctcgcctggg   2640
agggcagcta tcagtacatg gatctgcagc ctgaaggcta caacgatcgc catgcggtca   2700
atggcagctt ctacaagctg accttcgccc gacctccaa ggtgggcagc atcggcgact   2760
tcttctcgcg gccggagatc cgcttctata catcgtggat ggactggagc aaaaaactgg   2820
acaactacgc caacgatgac gcgttaggca gcaacggatt caaatcgggc ggcgaatggt   2880
cgttcggtat gcaaatggag acctggttct gacggcaacc ggggcgacag ggtaaataac   2940
acataaatat aaggttcgcg cgcgcctgcca cggctggcgc cgcccacgcc atatcatcat   3000
gcatttagag ggtactatgg attttgaaca gatttcccgc tcactgcttc ccctgctggg   3060
cggcaaggaa aatatcgcca gcgccgcgca ctgcgccacc cgcctgcggc tggtgctggt   3120
cgacgacgcg ctcgccgatc agcaggcgat tggcaaaatc gacggggtga aaggctgctt   3180
tcgcaatgcc ggacagatgc agatcatctt cggcaccggg gtggtcaata agtctatgc   3240
cgcctttatc caggccgcag gcatcagcga atcgagcaaa tccgaagccg ccgacctggc   3300
ggcgaaaaag ctgaacccgt tccagcgcat cgcccgcctg ctgtccaaca tcttcgtgcc   3360
gattattccg gccatcgtcg cctccggcct gctgatgggc ctgctgggga tggtgaaaac   3420
ctacggttgg gtcgacccga gcaacgctct ctatatcatg ctggatatgt gcagttcggc   3480
ggcgtttatc attctgccga tcctgatcgg ctttaccgcc gcacgcgaat tggcggtaa   3540
cccctatctg ggcgcgaccc tcggcggat cctcacccat ccggcgctga ccaacgcctg   3600
gggcgtcgcc gccggcttcc acaccatgaa tttcttcggc atcgaagtgg cgatgatcgg   3660
ctaccagggc accgtcttcc cggtgctgct ggcggtgtgg tttatgagca tggtcgagaa   3720
gcggctgcgc cgcgtgatcc ctgacgcgct ggacctgatc ctcactccgt tcctgacggt   3780
gattatctcc ggctttatcg ccctgctgct gatcggcccg gccggtcgcg cgctcggcga   3840
cggcatttcg tttatcctca gcacgcttat cagccatgcc ggctggctgg cgggcctgct   3900
gttcggcggc ctctattcgg tgatcgtcat taccggtatc catcacagct tccatgccat   3960
cgaggccgga ctgctgggca acccatcgat tggcgtcaac ttcctgctgc cgatctgggc   4020
gatggccaac gtcgcccagg gcggcgcctg ctttgcggtg tggtttaaaa ccaaagatgc   4080
caaaataaaa gccatcaccc tgccgtcggc gttttcggcg atgctgggga tcaccgaggc   4140
ggcaatcttc gggattaacc tgcgctttgt gaaaccgttt atcgccgcgc tggtgggcgg   4200
```

```
tgccgccggc ggcgcctggg tggtgtcgat gcacgtctac atgaccgcgg tgggcctgac    4260
ggcgatcccg gggatggcta tcgtgcaggc cagctcgctg ctgaactaca ttatcggaat    4320
ggcgatcgcc ttcgccgtgg ccttcgcgct ctctctgacg ctgaaataca aaacggacgc    4380
tgaataatgt cattaccgtc acgcctgcct gcgatcctgc aggccgttat gcagggccag    4440
ccgcaggcgc tggccgacag ccattatccg caatggcatc tggcgccggt caacggactg    4500
ctgaacgatc ctaacggctt tgccaggtc gccgggcgtt accacctgtt ttatcagtgg     4560
aacccgctcg cccgcgacca tacctataag tgctggggac actggagctc tgccgatctg    4620
ctgcactggc ggcacgaacc tatcgccctg atgccggatg aagagtatga ccgcaacggc    4680
tgctactctg gcagcgcggt cgagttcgag ggcgccctga ctctgtgcta caccggcaac    4740
gtgaaattcc ccgacggcgg gcgcaccgcc tggcaatgtc tggcgaccga gaatgccgat    4800
ggcaccttcc gcaagctggg gccggtgctg ccgctgccag aaggctatac cggccatgtg    4860
cgcgacccta agtgtggcg gcaggacggg cgctggtaca tggttcttgg ggcgcaggat     4920
gtgcaacagc gcggcaaagt gctgctgttt accgccagcg acctgcggga gtggcgcctg    4980
gtgggcgaga ttgccgggca cgacgtaaac ggcctggcga acgccggcta catgtgggag    5040
tgcccggatc tctttccgct ggcggacacc cacctgctga tctgctgccc gcaggggctg    5100
gcccgcgaag cgcagcgctt tctcaataccc tatccggcgg tgtggatggc aggccgcttc    5160
gacgccgaac gcgggatctt cgaccacggc ccgctgcacg agctggacag cggatttgag    5220
ttctacgcgc cgcagaccat gcaggccgat gatggccgcc gcctgctggt tggctggatg    5280
ggcgtccccg acggggacga gatgcatcag cccacccgcg cgcagggctg gatccatcag    5340
atgacctgcg tgcgtgagct ggagtggcag gctggcactc tgtatcagcg tccgctgcgc    5400
gagctggtcg ccctgcgcgg ggaagcccag ggctggtgcg gacagaccct gcccctcgcc    5460
ccgatggagc tggcctttga catcgccccc aacagcacgc tggggctgga ctttgccggc    5520
gccctgcagc tcaccgtcaa tcgcgacggc ctgcgtctgt cgcgtcgcgg cctgcagacg    5580
gcggagctgc atcaccgcta ctggcgcggc gaggcgcgac gcctgcggat ctttatcgac    5640
cgctccagcg tggagatttt catcaacgat ggcgaggggg tgatgagcag ccgcttcttc    5700
ccgggctatc cggggcagct catcttcagc ggtgcgacgc cggtagcatt ctgccgctgg    5760
ctgctgcggc catgcatggt agaataagcg ttttgctttc aggctcccgg gtgctgatga    5820
aaaccaaacg cgtaactatc aaagatatcg ccgaactggc gggcgtctcc aaagcgaccg    5880
ccagcctggt actcaacggt cgtggtaaag agctgcgcgt ggcgcaggag acgcgcgagc    5940
gcgtactggc gatcgctcgc gaacagcact atcagccgag cattcacgcg cgctcgctgc    6000
gcgataaccg cagccatacc attggtctgg tggtgccgga tcaccaac tacgggtttg      6060 ccgttttctc ccacgagctt gagacgctct gccgggaagc cggcgtgcag ctgcttatct    6120
cctgcaccga cgaaaaccct ggccaggaga gcgtggtggt caataacatg atcgcccgcc    6180
aggtcgacgg cctgattgtc gccccttgta tgcacagcga tgccgactat cagaaactca    6240
gcgaacagct gccggtggtg ctgtttgacc gctcccccag cgacagcgcc ctgccgctgg    6300
tgatgaccga ctcggtcacc ccaacggccg agctgatctc ccgtatcgcg cctcagcatg    6360
cggacgagtt ctggtttctc ggcggccagc cgcggctgtc gccgtcgcgc gaccggctgg    6420
cggggttcac ccagggcctg gcccaggcgg ggatcacgct gcgccctgag tgggtgatca    6480
acggcaacta ccaccccagc tccggctatg agatgttcgc ggcgctctgc gcgcggctgg    6540
ggcgtccgcc gaaggcgctc ttcaccgcgg cctgcgggct gctcgaaggg gtgctgcgct    6600
```

```
atatgagcca gcatcatctg ctggattcca atattcatct cgccagcttc gacgatcact   6660
atctgtatga ttcgctttcc ctgcgcattg ataccgtgca gcaggataat cgccagctgg   6720
cctggcactg ctacgatctg ctcagccagc tgatcgacgg tcaggcccg gagccgcttc    6780 agcgctacct gcccgccacc ctgcagattc gccatccctg acggcgcggt tggcaattag   6840
cgttttcgcc tagcgcgcgc cgcttgcctc agccagca gcgcgctggc gagcacccgc     6900
caaggccgat cgttaccggc cagcggtaag ccaccagcaa cgagggcaat ccaccatccg   6960
gcgccagcat caccagattc cagcccgcca gccccgcgtt gccgttcagc gcccggctta   7020
acatccacta gtagggca                                                 7038
```

<210> SEQ ID NO 6
<211> LENGTH: 924
<212> TYPE: DNA
<213> ORGANISM: Klebsiella pneumoniae(ATCC700721)
<220> FEATURE:
<221> NAME/KEY: gene
<222> LOCATION: (1)..(924)
<223> OTHER INFORMATION: scrK

<400> SEQUENCE: 6

```
atgaatggaa aaatctgggt actcggcgat gcggtcgtcg atctcctgcc cgatggagag   60
ggccgcctgc tgcaatgccc cggcggcgcg ccggccaacg tggcggtcgg cgtggcgcgg   120
ctcggcggtg acagcgggtt tatcggccgc gtcggcgacg atcccttcgg ccgttttatg   180
cgtcacaccc tggcgcagga gcaagtggat gtggactata tgcgcctcga tgcggcgcag   240
cgcacctcca cggtggtggt cgatctcgat agccacgggg agcgcacctt tacctttatg   300
gtccgtccga gcgccgacct gttccttcag cccgaggatc tcccgccgtt tgccgccggt   360
cagtggctgc acgtctgctc catcgctctc agcgcggagc cgagccgcag cacgacattc   420
gcggcgatgg aggcgataaa gcgcgccggg gctatgtca gcttcgaccc caatatccgc    480
agcgacctgt ggcaggatcc gcaggacctt cgcgactgtc tcgaccgggc gctggccctc   540
gccgacgcca taaactttc ggaagaggag ctggcgttta tcagcggcag cgacgacatc    600
gtcagcggca ccgcccggct gaacgcccgc ttccagccga cgctactgct ggtgacccag   660
ggtaaagcgg gggtccaggc cgccctgcgc gggcaggtta gccacttccc tgcccgcccg   720
gtggtggccg tcgataccac cggcgccggc gatgcctttg tcgccgggct actcgccggc   780
ctcgccgccc acggtatccc ggacaacctc gcagccctgg ctcccgacct cgcgctggcg   840
caaacctgcg gcgccctggc caccaccgcc aaaggcgcca tgaccgccct gccctacagg   900
gacgatcttc agcgctcgct gtga                                          924
```

<210> SEQ ID NO 7
<211> LENGTH: 1518
<212> TYPE: DNA
<213> ORGANISM: Klebsiella pneumoniae(ATCC700721)
<220> FEATURE:
<221> NAME/KEY: gene
<222> LOCATION: (1)..(1518)
<223> OTHER INFORMATION: scrY

<400> SEQUENCE: 7

```
atgtataaaa aacggaagtt agccattctt attgctttgc taaccggcac cgccgccgcc   60
catgggcaga cagacctgaa cagcattgaa gcgcgtctcg ccgccctgga aaaacgcctg   120
caggacgccg agacccgcgc cagcactgcc gaaagccgcg ccgcctcagc ggagcagaaa   180
gttcagcagt taacccagca gcagcagcaa acccaggcca ccacccagca ggtggccagg   240
```

```
cgcaccactc aactggaaga aaaagccgaa cggcccggcg gctttgagtt ccacggctat    300
gcgcgttccg gggtgatcat gaacgactcg gccgccagta ccaaatccgg cgcttatatg    360 accccccgccg gggagaccgg cggcgccatt ggtcgcctgg gcaaccaggc cgacaccta    420 gtggaaatga acctcgaaca taaacagacc ctggacaacg gggcgaccac ccgtttcaaa    480
gtgatggtgg ccgacggaca gaccacttat aacgactgga cggcaagcag cagcgatctg    540
aacgtgcgcc aggcgttcgt cgagctgggc aacctgccga ccttcgaagg cccgttcaga    600
ggctcgaccc tgtgggccgg gaaacgcttt gaccgcgaca acttcgacat ccactggatt    660
gactcggatg tggtgttcct cgccgggacc ggcggcggga tctacgacgt gaaatggaac    720
gacagcctgc gcagcaactt ctcgttatac ggccgcaact ttggcgatat cgccgacagc    780
agcaacagcg tgcagaacta tatcgtcagc atgaataact ttgccggccc ggtgcggatg    840
atggtcagcg ggatgcgggc gaaagataat gacgaccgcc aggacgcgaa cggcaatctg    900
gtgaaaggcg atgccgctaa caccgggggtt catgccctgc tgggcctgca caatgagagc    960
ttctatggcc tgcgcgacgg gaccagcaaa acggccctgc tgtacggcca cgggctgggc    1020
gccgaggtta aaggcatcgg ctccgacggc gcgctgcgcc cggggggccaa tacctggcgc    1080 ttcgccagct atggcaccac gccgctgagc gatcgctggt ttattgcccc ggccgtgctg    1140
gcgcagagca gtaaagatcg ttatgtcgat ggcgacagct atcagtgggc caccctcaac    1200
ctgcgtctga ttcaggaagt gacgcagaac ttcgccctcg cctgggaggg cagctatcag    1260
tacatggatc tgcagcctga aggctacaac gatcgccatg cggtcaatgg cagcttctac    1320
aagctgacct tcgccccgac cttcaaggtg ggcagcatcg gcgacttctt ctcgcggccg    1380
gagatccgct tctatacatc gtggatggac tggagcaaaa aactggacaa ctacgccaac    1440
gatgacgcgt taggcagcaa cggattcaaa tcgggcggcg aatggtcgtt cggtatgcaa    1500
atggagacct ggttctga                                                 1518

<210> SEQ ID NO 8
<211> LENGTH: 1371
<212> TYPE: DNA
<213> ORGANISM: Klebsiella pneumoniae(ATCC700721)
<220> FEATURE:
<221> NAME/KEY: gene
<222> LOCATION: (1)..(1371)
<223> OTHER INFORMATION: scrA

<400> SEQUENCE: 8
atggattttg aacagatttc ccgctcactg cttcccctgc tgggcggcaa ggaaaatatc     60
gccagcgccg cgcactgcgc cacccgcctg cggctggtgc tggtcgacga cgcgctcgcc    120
gatcagcagg cgattggcaa aatcgacggg gtgaaaggct gctttcgcaa tgccggacag    180
atgcagatca tcttcggcac cggggtggtc aataaagtct atgccgcctt tatccaggcc    240
gcaggcatca gcgaatcgag caaatccgaa gccgccgacc tggcggcgaa aaagctgaac    300
ccgttccagc gcatcgcccg cctgctgtcc aacatcttcg tgccgattat tccggccatc    360
gtcgcctccg gcctgctgat gggcctgctg ggatggtgaa aaacctacgg ttgggtcgac    420
ccgagcaacg ctctctatat catgctggat atgtgcagtt cggcggcgtt tatcattctg    480
ccgatcctga tcggctttac cgccgcacgc gaatttggcg taaccccta tctgggcgcg    540 accctcggcg ggatcctcac ccatccggcg ctgaccaacg cctggggcgt cgccgccggc    600
ttccacacca tgaatttctt cggcatcgaa gtggcgatga tcggctacca gggcaccgtc    660
ttcccggtgc tgctggcggt gtggtttatg agcatggtcg agaagcggct gcgccgcgtg    720
```

| | | | |
|---|---|---|---|
| atccctgacg | cgctggacct | gatcctcact | ccgttcctga cggtgattat ctccggcttt | 780 |
| atcgccctgc | tgctgatcgg | cccggccggt | cgcgcgctcg gcgacggcat ttcgtttatc | 840 |
| ctcagcacgc | ttatcagcca | tgccggctgg | ctggcgggcc tgctgttcgg cggcctctat | 900 |
| tcggtgatcg | tcattaccgg | tatccatcac | agcttccatg ccatcgaggc cggactgctg | 960 |
| ggcaacccat | cgattggcgt | caacttcctg | ctgccgatct gggcgatggc caacgtcgcc | 1020 |
| cagggcggcg | cctgctttgc | ggtgtggttt | aaaaccaaag atgccaaaat aaaagccatc | 1080 |
| accctgccgt | cggcgttttc | ggcgatgctg | gggatcaccg aggcggcaat cttcgggatt | 1140 |
| aacctgcgct | ttgtgaaacc | gtttatcgcc | gcgctggtgg gcggtgccgc cggcggcgcc | 1200 |
| tgggtggtgt | cgatgcacgt | ctacatgacc | gcggtgggcc tgacggcgat cccggggatg | 1260 |
| gctatcgtgc | aggccagctc | gctgctgaac | tacattatcg gaatggcgat cgccttcgcc | 1320 |
| gtggccttcg | cgctctctct | gacgctgaaa | tacaaaacgg acgctgaata a | 1371 |

<210> SEQ ID NO 9
<211> LENGTH: 1401
<212> TYPE: DNA
<213> ORGANISM: Klebsiella pneumoniae(ATCC700721)
<220> FEATURE:
<221> NAME/KEY: gene
<222> LOCATION: (1)..(1401)
<223> OTHER INFORMATION: scrB

<400> SEQUENCE: 9

| | | | |
|---|---|---|---|
| atgtcattac | cgtcacgcct | gcctgcgatc | ctgcaggccg ttatgcaggg ccagccgcag | 60 |
| gcgctggccg | acagccatta | tccgcaatgg | catctggcgc cggtcaacgg actgctgaac | 120 |
| gatcctaacg | gcttttgcca | ggtcgccggg | cgttaccacc tgttttatca gtggaacccg | 180 |
| ctcgcccgcg | accataccta | taagtgctgg | ggacactgga gctctgccga tctgctgcac | 240 |
| tggcggcaca | aacctatcgc | cctgatgccg | gatgaagagt atgaccgcaa cggctgctac | 300 |
| tctggcagcg | cggtcgagtt | cgagggcgcc | ctgactctgt gctacaccgg caacgtgaaa | 360 |
| ttccccgacg | gcgggcgcac | cgcctggcaa | tgtctggcga ccgagaatgc cgatggcacc | 420 |
| ttccgcaagc | tggggccggt | gctgccgctg | ccagaaggct ataccggcca tgtgcgcgac | 480 |
| cctaaagtgt | ggcggcagga | cgggcgctgg | tacatggttc ttggggcgca ggatgtgcaa | 540 |
| cagcgcggca | aagtgctgct | gtttaccgcc | agcgacctgc gggagtggcg cctggtgggc | 600 |
| gagattgccg | gcacgacgt | aaacggcctg | gcgaacgccg gctacatgtg ggagtgcccg | 660 |
| gatctctttc | cgctggcgga | cacccacctg | ctgatctgct gcccgcaggg gctggcccgc | 720 |
| gaagcgcagc | gctttctcaa | tacctatccg | gcggtgtgga tggcaggccg cttcgacgcc | 780 |
| gaacgcggga | tcttcgacca | cggcccgctg | cacgagctgg acagcggatt tgagttctac | 840 |
| gcgccgcaga | ccatgcaggc | cgatgatggc | gcgccgcctg ctggttggctg gatgggcgtc | 900 |
| cccgacgggg | acgagatgca | tcagcccacc | cgcgcgcagg gctggatcca tcagatgacc | 960 |
| tgcgtgcgtg | agctggagtg | gcaggctggc | actctgtatc agcgtccgct gcgcgagctg | 1020 |
| gtcgccctgc | gcggggaagc | ccagggctgg | tgcggacaga ccctgcccct cgccccgatg | 1080 |
| gagctggcct | tgacatcgc | ccccaacagc | acgctggggc tggactttgc cggcgccctg | 1140 |
| cagctccaccg | tcaatcgcga | cggcctgcgt | ctgtcgcgtc gcggcctgca gacggcggag | 1200 |
| ctgcatcacc | gctactggcg | cggcgaggcg | cgacgcctgc ggatctttat cgaccgctcc | 1260 |
| agcgtggaga | ttttcatcaa | cgatggcgag | ggggtgatga gcagccgctt cttcccgggc | 1320 |
| tatccggggc | agctcatctt | cagcggtgcg | acgccggtag cattctgccg ctggctgctg | 1380 |

| | |
|---|---:|
| cggccatgca tggtagaata a | 1401 |

<210> SEQ ID NO 10
<211> LENGTH: 1005
<212> TYPE: DNA
<213> ORGANISM: Klebsiella pneumoniae(ATCC700721)
<220> FEATURE:
<221> NAME/KEY: gene
<222> LOCATION: (1)..(1005)
<223> OTHER INFORMATION: scrR

<400> SEQUENCE: 10

| | |
|---|---:|
| atgaaaacca aacgcgtaac tatcaaagat atcgccgaac tggcgggcgt ctccaaagcg | 60 |
| accgccagcc tggtactcaa cggtcgtggt aaagagctgc gcgtggcgca ggagacgcgc | 120 |
| gagcgcgtac tggcgatcgc tcgcgaacag cactatcagc cgagcattca cgcgcgctcg | 180 |
| ctgcgcgata accgcagcca taccattggt ctggtggtgc cggagatcac caactacggg | 240 |
| tttgccgttt ctcccacga gcttgagacg ctctgccggg aagccggcgt gcagctgctt | 300 |
| atctcctgca ccgacgaaaa ccctggccag gagagcgtgg tggtcaataa catgatcgcc | 360 |
| cgccaggtcg acggcctgat tgtcgcccct tgtatgcaca gcgatgccga ctatcagaaa | 420 |
| ctcagcgaac agctgccggt ggtgctgttt gaccgctccc ccagcgacag cgccctgccg | 480 |
| ctggtgatga ccgactcggt caccccaacg gccgagctga tctcccgtat cgcgcctcag | 540 |
| catgcggacg agttctggtt tctcggcggc cagccgcggc tgtcgccgtc gcgcgaccgg | 600 |
| ctggcggggt tcacccaggg cctggcccag gcggggatca cgctgcgccc tgagtgggtg | 660 |
| atcaacggca actaccaccc cagctccggc tatgagatgt tcgcggcgct ctgcgcgcgg | 720 |
| ctggggcgtc cgccgaaggc gctcttcacc gcggcctgcg ggctgctcga aggggtgctg | 780 |
| cgctatatga gccagcatca tctgctggat ccaatattc atctcgccag cttcgacgat | 840 |
| cactatctgt atgattcgct ttccctgcgc attgataccg tgcagcagga taatcgccag | 900 |
| ctggcctggc actgctacga tctgctcagc cagctgatcg acggtcaggc cccggagccg | 960 |
| cttcagcgct acctgccgc cacctgcag attcgccatc cctga | 1005 |

<210> SEQ ID NO 11
<211> LENGTH: 7219
<212> TYPE: DNA
<213> ORGANISM: Erwinia carotovora(ATCCBAA-672)

<400> SEQUENCE: 11

| | |
|---|---:|
| gtgcaccccc tgaccgtaat agtgaaggga aaattcgcta taaatatcaa caagccagac | 60 |
| gacaaccaat aaagcccata tcgcccatat tccccaaagc aggttgtaat tacgcaccgg | 120 |
| gataaaccca gaaagaggtg gggtaacgca tatccttctc cattcgtcct tttttgcagct | 180 |
| taatttccag attaattctg ccacgcccc ataactatcg gatggtaagc ccttttgttt | 240 |
| agtcctatga ccgtggcaac gtgatgacta tcgcataaat tttcaccaac acggtgtgga | 300 |
| aatgtaagtt ttattgatgt gggtgcgtct ctgcggtgaa gggtattgct tagctaaacc | 360 |
| gattcttcta ttttagcaaa tagtctgact atcgttgata agagtaactt tatggcaaac | 420 |
| aaaatttggg tcatgggcga cgccgttgtc gatctcatcc ggaagatac ggaacgctat | 480 |
| ctgaaatgtc ctggcggtgc gccagccaat gtcgcggttg cattgccag actgggggga | 540 |
| aacagcgcct ttgtcggtcg cgtcggtgac gatgttttg gccatttct aaaaacggtg | 600 |
| ctggaagaag aaaacgtcga tacccactac atggcgtacg acagacacca ccgcacatca | 660 |
| accgtggtcg tgagcctcga tgacgcgggt gaacgcacct tcacgtttat ggtacgcccg | 720 |

```
agtgccgacc tgttcctaca accggaagat ctgccggtat tcaaccggag agaatggctg    780
catctctgtt ctatcgcact gtcgcaggaa ccgtcgcgca gtaccgcgtt tgaggcaatg    840
cgacagatta agccgcgct ggggcgcgtt tgcttcgacc ccaatatccg tgacgacctc     900
tggcaaagcg agcaggaact gcgcgactgc ctgacacaag cgctgatgct ggccgatgtg    960
gtgaaactgt cgtgtgaaga gctgaccttt ctctgtccaa catctgatgt tgaagaaggg    1020
atccagcaat tcatgctgcg ctaccccact cggctattgc tggtgacact gggcagcgaa    1080
ggtgtctggc tgcacgatcg ccaccagcta caacactttg ctgcccctc ggtgacacct     1140 gtcgatacca cgggtgcagg ggatgccttc gttgccggtt tgctgcacgg tctggcggaa    1200
tatgatgatt tgtcacagcc gctgagctgg gatccgatta tcgagcaggc gcaacggtgc    1260
ggcgcactag ctactacggc aaaaggcgcg atgacggcgc ttccctatgc ccagcagttg    1320
tacacactcc ccttagccaa ggtctaatcc cccctcgtt taatacgatt accgcccggt     1380
tttgtagtca ggatcacagt tacagaatcg ggtgagtgaa atttcttgct aacccttctg    1440
ctggctttta ttttcctcaa gaaaaaccgg tttagcaatt tagctaaaca tgagaattcc    1500
aaaaacaata aatctccttc acgacagaaa cgaaaaaatg aaaccaagcc accttgctgt    1560
gacgatagga ttattactct ccgccccgtt ttatgtttct gctgccaaca ccgacagtat    1620
cgaagaccgc ctgaacgcaa tggaacaacg cttgcaacag gctgaagccc gcgctcaggc    1680
cgccgaagcc agagccaatg ctgctgaaaa gcaaacccag cagctagcaa cccgcaccac    1740
ccaaaccgaa caaaaaaccc agcaggtgga gcagcgcaca acggcgctgg ccaaacagaa    1800
gtcattctcc gatggattcg aattccacgg ctacgcgcgt tccggcctgt cgatcaatga    1860
ttccgccacc agtgccaaaa ccgatatccg gccgggcatg tcccctgccg gtcagacagg    1920
cgggcatatt ggtcgtttgg gtaatgaaga cgacacctac gtcgagctca aactagagca    1980
caaacagaag ctggataacg cgcaaccac ccgattcaag gtgatgatgg cggacggtca     2040
gcgcagctat aacgactgga cggcgaccac cagcgatctg aacatccgcg aagccttcgt    2100
cgagctgggc tcactgccga cttttcaccga tgtctttaag gacactacgc tgtgggcggg    2160
taaacgcttc gatcgcgata acttcgatat ccactggctg gatagcgatg tcgtgttcct    2220
cgccggtact ggcggcggga tctatgacgt gaaatgggca gatagcgcca agagtaactt    2280
ctcgctgtat ggccgcagcc tcggtgaaat cacctcgctg gataacgaca tcaaaaacta    2340
cgtctttacc gccaacaact acgttgggcc attccagttc atgctgagcg gattaaccgc    2400
gaagaacaat gatgtaaaag agaacactgg cacaagccgc gataacatca ccgtcaccaa    2460
taccaatgcg ggcggcaaag gctatcacgc gatggtggct taccacgcg acagcttcta     2520 cggcttacgc gacgggacat cgaaaactgc gatcctctac ggccacgggc taggcggcga    2580
agtgaagagt atcggttccg acggtaacct caccaacgac gccaacacat ggcgctttgc    2640
gacctacggc acaacagcgc tgaacaagac ctggagcttc gcaccgtcca ttctggcgca    2700
aaccagcaaa gaccgttacg tcagcggcga tagctacgaa tgggtgacct ttaatgcgcg    2760
cctgattcag gaaatcaccg aaaactttgc actggcctat gaaggcagct atcaatacat    2820
gggcctcgat ccgcgcggtt atcggagcct gaatcaggtg agcggcggct tctataaact    2880
gaccttcgcg cctacattca aggttggcga tatcggcaac ttcttcagcc gtcctgaact    2940
acgcgtgttt gccagctaca tggactggga taaacgactg gataactact ccaacgatga    3000
tacgttcggc tccaccggct ttaaagcagg cggcgaatgg aactttggca tccagatgga    3060
aacctggttc tgatcattgg ctagccttgg cgtcgatgac acgctaatcg acgccaaaga    3120
```

```
aactgcatat cctattgaaa aagaggaata acatggatat caatgctact gccgccgcgc    3180 taatcccct  tctcggtggg aaagaaaaca tcgccagcgc ggcccactgt gcgacccgtc    3240
tacgtctggt attgaatgac gacagcctgg ccgacaagaa agcgatcgag aacgttgacg    3300
gcgtgaaagg atgcttccag aacgccggac aaatgcagat tattttcggc accggactgg    3360
ttaacaaagt gtatgccgag ttcattaaag ccgcaggtat cagcgaatca agcaaatctg    3420
aagccgcctc tatcgcggcg agaaagctga atccgctgca acgtctggcg cgtctgctat    3480
cgaacatctt cgtccctata atgccagcga ttatcgcttc cggcctgttg atggggctgc    3540
tcggcatgat caagacctac ggctgggtag atgccaacag cgcgatcttt gtgatgctgg    3600
atatgttcag ctccgctgcc tttattatcc tgcctgttct gatcggtttt accgctgcac    3660
gggaattcgg cggcaacccc tatctgggtg caacgctggg cggcattctg acccatcctg    3720
cgctgaccaa cgcttggggc gtggcggggg gcttccagac catgcatttc ttcggcatgg    3780
acattgccat gattggctat cagggtaccg tattcccagt actgctggcc gtctggttca    3840
tgagtcttgt ggaaaaacgc ctgcgtaaag tcgtaccgga cgcactggac atcatcgtta    3900
cgcctttcct gacggtcatc atctccggct tcgtcgcgat gctgctcatc ggcccagcag    3960
gacgcgcgct tggcgatggt atttctctcg tcctcagcac gttgattgct catgctggct    4020
ggttcgcggg tttactgttc ggtggcctct actccgtcat cgtgatcacc ggcgttcacc    4080
acagcttcca tgcgattgaa gccggactac tcggcaaccc gaatatcggc gtcaacttcc    4140
tgctgccaat ttgggcaatg gcgaacgtgg cgcaggcgg cgcgtgtctg gcggtctact    4200
ttaaaacgcg tgacgccaaa accagagcga ttgccgttcc ggcggggctt tcctgtctgc    4260
tgggtatcac cgaagcagcg atctttggta tcaacctgcg tttcattaag ccgttcctcg    4320
cagcactggc gggtggtgcg ctcggtggcg catgggtcgt cttcaatcac gtcaatatga    4380
cggcggtcgg gctgaccggt tttccggggc tagccattgt gcaaggtggc tcgatgctta    4440
actacctgat tgggatgttg attgcattcg gtgccgcctt tgtcatttcc ttattgctga    4500
aatacaaaac ggatagcgaa taatgaagga agtccactta gtaaaacgca tggcgcacgc    4560
cctgatgtca ggtcactcac ggaaacagga agacccatat cgcccggaat ggcatctgtc    4620
accgtgtgtg ggtctgctta acgatccgaa cggatttatt catcacaacg ggcgttacca    4680
tctgttttat cagtggaatc ctttggcctg tgcccacgga gcaaaattct gggggcactg    4740
gagttccgcc gatctggtga actggaagca tgaacccgtc gcgctggtgc cgagcgaaag    4800
ctatgaaagc cacggctgct actccggttc tgccgtcgta gatcacggtg cgatcacgct    4860
gatttacacg ggtaacgtca aatacgacga tggctcacgc accgcgtttc agtgtctcgc    4920
ccgcgaaaat cctaacggtg aatacgacaa gctgggagcg gttctgacgc tcccagacgg    4980
ctacactggc cacgttcgcg atccgaaagt gtggcgtcat ggtgaccact ggtacatggt    5040
gctcggcgca caggatctcg atcttcaggg gaaggtcgtg ctctatcgtt ctgccgatct    5100
gctggcgtgg gaaaagatcg ccgagatcgc cggctctcgt ttgggcgggc tcggtgattt    5160
tggttatatg tgggagtgtc cagacttgtt cccgctggat ggcgaagaca tactgatttg    5220
ctgcccacaa ggcgttcccg ctgaagatga acgctacctg aatacctttc aggcgggcta    5280
tttcattggc tcactcgact acgaaaacgg cgattactcg catcagggtt tccatgaact    5340
ggatctcggc tttgagtttt acgccccaca aaccacgctg agtgaagacg ggcgacgcct    5400
gctgtttggc tggatgtcga ttcctgacga caatgaattt tttgaaccga cgatcgagca    5460
cggctggatt catactatga cctgcgcgcg tgaactcacg ctgcatgacg atcgcgttta    5520
```

```
tcaacgtcct gcgcgcgaat tacaacagtt gcgcagacag cattacacct ggcgtggtgc      5580
agcagactac gcgtcgccgc tacccattag tagcgcagaa gtgctcatca ccgttcaggg      5640
ggaattccag ctcaatcttg cctcccagct tgttctctgt tgggacggtg aacgcgtaac      5700
gataagccga cgcaaccgac gcacaggcga acctgaacat cgctactggc gcggcgaccct     5760 gcgtcaatta cagatattgt gcgatcgctc cagcgttgaa attttttatca acgatggcga     5820 ggccgtgatg tctgcacgaa cttccccgga aagcgaggcg accatgacgt tcagcggctc      5880
tgggcaatta acgctacaac actggctgtt agcgccatgc gtgatagaat aactttcctt      5940
ttttctgata gcagacctcg cggtgaaacc gactaaacgc ataacaatca gtgacatcgc      6000
cgcgctggcc ggtgtatcaa aatctaccgc cagcctggtg ctgaacggcc gcagcaaaga      6060
gttccgcgtt tctgatgaaa cgcgcgatcg cattttagcc gtcgcacacg agcagcgtta      6120
tcagcccagt attcacgcac gttcactgcg ttcctcacgc agtaacacgc tggggctggt      6180
ggtgccagaa atgaccaact acggcttttgc cgtgatttcc cgcgaactgg agatgcggtg      6240
ccgcgaagct gggctacagt tgctaattgc ctgtaccgat gaaaatgcca gtcaggagat      6300
gatggcggtc aacagtctgg tacagcgcca ggtcgatggc ctgattgtcg cttccagcct      6360
gctgagtgat atcgagtatc agaaaattaa tcagcagctg cccgtcgtgc aatttgaccg      6420
gattattggt gattccacac tgccgatggt catttccgaa gcggtagaat ccacagcaga      6480
aatggtcgag cgtatcgccc gccagcatcg tgatgaattt tatttccttg gcggccagcc      6540
gcgaatttcc ccgactcgcc accgtctgga aggctttcag cttgggttga cgcgtgccgg      6600
tatcgagtgc cagccggagt ggattcttca tggcaactac caccccagcg caggttatga      6660
aatgtttgct caactgtgtg cgacgctggg tcgcccgcca aaagcactgt tgttgccgc       6720 ctgtggcctg atggaaggcg tgctgcgtta tatgaaccag cataacctga tggaaagcgg      6780
catccgtctg tgctgctttg acgatcacta tctgtttgat tgtttaccgc tgaagatcga      6840
taccgtggcg caggattgtg aaaatctggc acgcaacagc tttgaaatga ttacgagttt      6900
gattgcacaa cagccgcttg aagaagatcg gcgctatatc ccgacgcgga ttcactggcg      6960
tcatcctgac tcgcgggcat gactcgcgac atagcccaac acacttcacc agcaggtaga      7020
acgtaaaaag ggaacgcggt tagcgtcgct tcttagagca tcgcaccaca ttcccttttg      7080
aatcgatcag ccgttactta gcggcggcag attccgcgcc aaccagaccc accttgaggt      7140
agcccgcttt acgcagtgaa tccatcacgc tcatgatggt ttcataatcg acgcttttat      7200
ctgcctgact agtagggca                                                   7219

<210> SEQ ID NO 12
<211> LENGTH: 936
<212> TYPE: DNA
<213> ORGANISM: Erwinia carotovora(ATCCBAA-672)
<220> FEATURE:
<221> NAME/KEY: gene
<222> LOCATION: (1)..(936)
<223> OTHER INFORMATION: scrK

<400> SEQUENCE: 12
atggcaaaca aaatttgggt catgggcgac gccgttgtcg atctcatccc ggaagatacg        60
gaacgctatc tgaaatgtcc tggcggtgcg ccagccaatg tcgcggttgg cattgccaga       120
ctggggggaa acagcgcctt tgtcggtcgc gtcggtgacg atgttttggg ccattttcta       180
aaaacggtgc tggaagaaga aaacgtcgat acccactaca tggcgtacga cagacaccac       240
cgcacatcaa ccgtggtcgt gagcctcgat gacgcgggtg aacgcacctt cacgtttatg       300
```

```
gtacgcccga gtgccgacct gttcctacaa ccggaagatc tgccggtatt caaccggaga      360
gaatggctgc atctctgttc tatcgcactg tcgcaggaac cgtcgcgcag taccgcgttt      420
gaggcaatgc gacagattaa agccgcgctg gggcgcgttt gcttcgaccc caatatccgt      480
gacgacctct ggcaaagcga gcaggaactg cgcgactgcc tgacacaagc gctgatgctg      540
gccgatgtgg tgaaactgtc gtgtgaagag ctgacctttc tctgtccaac atctgatgtt      600
gaagaaggga tccagcaatt catgctgcgc taccccactc ggctattgct ggtgacactg      660
ggcagcgaag gtgtctggct gcacgatcgc caccagctac aacactttgc tgcccctcg       720 gtgacacctg tcgataccac gggtgcaggg gatgccttcg ttgccggttt gctgcacggt      780
ctggcggaat atgatgattt gtcacagccg ctgagctggg atccgattat cgagcaggcg      840
caacggtgcg gcgcactagc tactacggca aaaggcgcga tgacggcgct tccctatgcc      900
cagcagttgt acacactccc cttagccaag gtctaa                                936

<210> SEQ ID NO 13
<211> LENGTH: 1536
<212> TYPE: DNA
<213> ORGANISM: Erwinia carotovora(ATCCBAA-672)
<220> FEATURE:
<221> NAME/KEY: gene
<222> LOCATION: (1)..(1536)
<223> OTHER INFORMATION: scrY

<400> SEQUENCE: 13
atgaaaccaa gccaccttgc tgtgacgata ggattattac tctccgcccc gttttatgtt       60
tctgctgcca acaccgacag tatcgaagac cgcctgaacg caatggaaca acgcttgcaa      120
caggctgaag cccgcgctca ggccgccgaa gccagagcca atgctgctga aaagcaaacc      180
cagcagctag caaccgcac cacccaaacc gaacaaaaaa cccagcaggt ggagcagcgc       240
acaacggcgc tggccaaaca gaagtcattc tccgatggat cgaattcca cggctacgcg       300 cgttccggcc tgtcgatcaa tgattccgcc accagtgcca aaaccgatat cgggccgggc      360
atgtcccctg ccggtcagac aggcgggcat attggtcgtt tgggtaatga agacgacacc      420
tacgtcgagc tcaaactaga gcacaaacag aagctggata acggcgcaac caccgattc       480 aaggtgatga tggcggacgg tcagcgcagc tataacgact ggacggcgac caccagcgat      540
ctgaacatcc gcgaagcctt cgtcgagctg ggctcactgc cgactttcac cgatgtcttt      600
aaggacacta cgctgtgggc gggtaaacgc ttcgatcgcg ataacttcga tatccactgg      660
ctggatagcg atgtcgtgtt cctcgccggt actggcggcg ggatctatga cgtgaaatgg      720
gcagatagcg ccaagagtaa cttctcgctg tatggccgca gcctcggtga atcaccctcg      780
ctggataacg acatcaaaaa ctacgtcttt accgccaaca actacgttgg gccattccag      840
ttcatgctga gcggattaac cgcgaagaac aatgatgtaa agagaacac tggcacaagc       900 cgcgataaca tcaccgtcac caataccaat gcgggcggca aaggctatca cgcgatggtg      960
gcttaccacg cgacagcttc tacggcttta cgcgacggga catcgaaaac tgcgatcctc     1020
tacgccacgg gctaggcgg cgaagtgaag agtatcggtt ccgacggtaa cctcaccaac     1080
gacgccaaca catggcgctt tgcgacctac ggcacaacag cgctgaacaa gacctggagc     1140
ttcgcaccgt ccattctggc gcaaaccagc aaagaccgtt acgtcagcgg cgatagctac     1200
gaatgggtga cctttaatgc gcgcctgatt caggaaatca ccgaaaactt tgcactggcc     1260
tatgaaggca gctatcaata catgggcctc gatccgcgcg ttatcggag cctgaatcag     1320 gtgagcggcg gcttctataa actgaccttc gcgcctacat tcaaggttgg cgatatcggc     1380
```

| | | |
|---|---|---|
| aacttcttca gccgtcctga actacgcgtg tttgccagct acatggactg ggataaacga | 1440 | |
| ctggataact actccaacga tgatacgttc ggctccaccg gctttaaagc aggcggcgaa | 1500 | |
| tggaactttg gcatccagat ggaaacctgg ttctga | 1536 | |

<210> SEQ ID NO 14
<211> LENGTH: 1371
<212> TYPE: DNA
<213> ORGANISM: Erwinia carotovora(ATCCBAA-672)
<220> FEATURE:
<221> NAME/KEY: gene
<222> LOCATION: (1)..(1371)
<223> OTHER INFORMATION: scrA

<400> SEQUENCE: 14

| | | |
|---|---|---|
| atggatatca atgctactgc cgccgcgcta atccccttc tcggtgggaa agaaaacatc | 60 | |
| gccagcgcgg cccactgtgc gacccgtcta cgtctggtat tgaatgacga cagcctggcc | 120 | |
| gacaagaaag cgatcgagaa cgttgacggc gtgaaaggat gcttccagaa cgccggacaa | 180 | |
| atgcagatta ttttcggcac cggactggtt aacaaagtgt atgccgagtt cattaaagcc | 240 | |
| gcaggtatca gcgaatcaag caaatctgaa gccgcctcta tcgcggcgag aaagctgaat | 300 | |
| ccgctgcaac gtctggcgcg tctgctatcg aacatcttcg tccctataat gccagcgatt | 360 | |
| atcgcttccg gcctgttgat ggggctgctc ggcatgatca agacctacgg ctgggtagat | 420 | |
| gccaacagcg cgatctttgt gatgctggat atgttcagct ccgctgcctt tattatcctg | 480 | |
| cctgttctga tcggttttac cgctgcacgg gaattcggcg gcaacccta tctgggtgca | 540 | |
| acgctgggcg gcattctgac ccatcctgcg ctgaccaacg cttggggcgt ggcgggggc | 600 | |
| ttccagacca tgcatttctt cggcatggac attgccatga ttggctatca gggtaccgta | 660 | |
| ttcccagtac tgctggccgt ctggttcatg agtcttgtgg aaaaacgcct gcgtaaagtc | 720 | |
| gtaccggacg cactggacat catcgttacg ccttttcctga cggtcatcat ctccggcttc | 780 | |
| gtcgcgatgc tgctcatcgg cccagcagga cgcgcgcttg gcgatggtat ttctctcgtc | 840 | |
| ctcagcacgt tgattgctca tgctggctgg ttcgcgggtt tactgttcgg tggcctctac | 900 | |
| tccgtcatcg tgatcaccgg cgttcaccac agcttccatg cgattgaagc cggactactc | 960 | |
| ggcaacccga atatcggcgt caacttcctg ctgccaattt gggcaatggc gaacgtggcg | 1020 | |
| cagggcggcg cgtgtctggc ggtctacttt aaaaacgcgtg acgccaaaac cagagcgatt | 1080 | |
| gccgttccgg cggggcttc ctgtctgctg gtataccg aagcagcgat ctttggtatc | 1140 | |
| aacctgcgtt tcattaagcc gttcctcgca gcactggcgg tggtgcgct cggtggcgca | 1200 | |
| tgggtcgtct tcaatcacgt caatatgacg gcggtcgggc tgaccggttt tccgggcta | 1260 | |
| gccattgtgc aaggtggctc gatgcttaac tacctgattg ggatgttgat tgcattcggt | 1320 | |
| gccgcctttg tcatttcctt attgctgaaa tacaaaacgg atagcgaata a | 1371 | |

<210> SEQ ID NO 15
<211> LENGTH: 1410
<212> TYPE: DNA
<213> ORGANISM: Erwinia carotovora(ATCCBAA-672)
<220> FEATURE:
<221> NAME/KEY: gene
<222> LOCATION: (1)..(1410)
<223> OTHER INFORMATION: scrB

<400> SEQUENCE: 15

| | | |
|---|---|---|
| atgaaggaag tccacttagt aaaacgcatg gcgcacgccc tgatgtcagg tcactcacgg | 60 | |
| aaacaggaag acccatatcg cccggaatgg catctgtcac cgtgtgtggg tctgcttaac | 120 | |

```
gatccgaacg gatttattca tcacaacggg cgttaccatc tgttttatca gtggaatcct    180
ttggcctgtg cccacggagc aaaattctgg gggcactgga gttccgccga tctggtgaac    240
tggaagcatg aacccgtcgc gctggtgccg agcgaaagct atgaaagcca cggctgctac    300
tccggttctg ccgtcgtaga tcacggtgcg atcacgctga tttacacggg taacgtcaaa    360
tacgacgatg gctcacgcac cgcgtttcag tgtctcgccc gcgaaaatcc taacggtgaa    420
tacgacaagc tgggagcggt tctgacgctc ccagacggct acactggcca cgttcgcgat    480
ccgaaagtgt ggcgtcatgg tgaccactgg tacatggtgc tcggcgcaca ggatctcgat    540
cttcagggga aggtcgtgct ctatcgttct gccgatctgc tggcgtggga aagatcgcc     600 gagatcgccg gctctcgttt gggcgggctc ggtgattttg gttatatgtg ggagtgtcca    660
gacttgttcc cgctggatgg cgaagacata ctgatttgct cccacaagg cgttcccgct     720 gaagatgaac gctacctgaa tacctttcag gcgggctatt tcattggctc actcgactac    780
gaaaacggcg attactcgca tcagggtttc catgaactgg atctcggctt tgagttttac    840
gccccacaaa ccacgctgag tgaagacggg cgacgcctgc tgtttggctg gatgtcgatt    900
cctgacgaca atgaattttt tgaaccgacg atcgagcacg gctggattca tactatgacc    960
tgcgcgcgtg aactcacgct gcatgacgat cgcgtttatc aacgtcctgc gcgcgaatta   1020
caacagttgc gcagacagca ttacacctgg cgtggtgcag cagactacgc gtcgccgcta   1080
cccattagta gcgcagaagt gctcatcacc gttcaggggg aattccagct caatcttgcc   1140
tcccagcttg ttctctgttg ggacggtgaa cgcgtaacga taagccgacg caaccgacgc   1200
acaggcgaac ctgaacatcg ctactggcgc ggcgacctgc gtcaattaca gatattgtgc   1260
gatcgctcca gcgttgaaat ttttatcaac gatggcgagg ccgtgatgtc tgcacgaact   1320 ttccccggaaa gcgaggcgac catgacgttc agcggctctg ggcaattaac gctacaacac   1380
tggctgttag cgccatgcgt gatagaataa                                     1410
```

<210> SEQ ID NO 16
<211> LENGTH: 1020
<212> TYPE: DNA
<213> ORGANISM: Erwinia carotovora(ATCCBAA-672)
<220> FEATURE:
<221> NAME/KEY: gene
<222> LOCATION: (1)..(1020)
<223> OTHER INFORMATION: scrR

<400> SEQUENCE: 16

```
gtgaaaccga ctaaacgcat aacaatcagt gacatcgccg cgctggccgg tgtatcaaaa     60
tctaccgcca gcctggtgct gaacggccgc agcaaagagt ccgcgtttc tgatgaaacg    120 cgcgatcgca ttttagccgt cgcacacgag cagcgttatc agcccagtat tcacgcacgt    180
tcactgcgtt cctcacgcag taacacgctg gggctggtgg tgccagaaat gaccaactac    240
ggctttgccg tgatttcccg cgaactggag atgcggtgcc gcgaagctgg gctacagttg    300
ctaattgcct gtaccgatga aaatgccagt caggagatga tggcggtcaa cagtctggta    360
cagcgccagg tcgatggcct gattgtcgct tccagcctgc tgagtgatat cgagtatcag    420
aaaattaatc agcagctgcc cgtcgtgcaa tttgaccgga ttattggtga ttccacactg    480
ccgatggtca tttccgaagc ggtagaatcc acagcagaaa tggtcgagcg tatcgcccgc    540
cagcatcgtg atgaattta tttccttggc ggccagccgc gaatttcccc gactcgccac    600
cgtctggaag gctttcagct tgggttgacg cgtgccggta tcgagtgcca gcggagtgg    660 attcttcatg gcaactacca ccccagcgca ggttatgaaa tgtttgctca actgtgtgcg    720
```

| | | |
|---|---|---|
| acgctgggtc gcccgccaaa agcactgttt gttgccgcct gtggcctgat ggaaggcgtg | 780 |
| ctgcgttata tgaaccagca taacctgatg gaaagcggca tccgtctgtg ctgctttgac | 840 |
| gatcactatc tgtttgattg tttaccgctg aagatcgata ccgtggcgca ggattgtgaa | 900 |
| aatctggcac gcaacagctt tgaaatgatt acgagtttga ttgcacaaca gccgcttgaa | 960 |
| gaagatcggc gctatatccc gacgcggatt cactggcgtc atcctgactc gcgggcatga | 1020 |

<210> SEQ ID NO 17
<211> LENGTH: 10526
<212> TYPE: DNA
<213> ORGANISM: Artificial Sequence
<220> FEATURE:
<223> OTHER INFORMATION: pAscrKP

<400> SEQUENCE: 17

| | | |
|---|---|---|
| agatgcgtag tcagcgtcag cttctggtac cgatcgtaaa tatcgccaaa actgggttc | 60 |
| atcgcgctac gcactccttt acctttggcc accgcgcgg ggctaaccgc gacctggtga | 120 |
| actatacccta agcgggtggg gaaggaaaag tccagatctg gagtggcgaa atattccgcc | 180 |
| tggctcacat tttttaccct cgcctccctg tttcgtgacc caatcgttcc gcttaccggt | 240 |
| gggctgtgct ttaatgagct aaaccggttt aataaagttt agcttagagg agcttgtcgt | 300 |
| atgaatggaa aaatctgggt actcggcgat gcggtcgtcg atctcctgcc cgatggagag | 360 |
| ggccgcctgc tgcaatgccc cggcggcgcg ccggccaacg tggcggtcgg cgtggcgcgg | 420 |
| ctcggcggtg acagcgggtt tatcggccgc gtcggcgacg atcccttcgg ccgttttatg | 480 |
| cgtcacaccc tggcgcagga gcaagtggat gtggactata tgcgcctcga tgcggcgcag | 540 |
| cgcacctcca cggtggtggt cgatctcgat agccacgggg agcgcacctt tacctttatg | 600 |
| gtccgtccga gcgccgacct gttccttcag cccgaggatc tcccgccgtt tgccgccggt | 660 |
| cagtggctgc acgtctgctc catcgctctc agcgcggagc cgagccgcag cacgacattc | 720 |
| gcggcgatgg aggcgataaa gcgcgccggg ggctatgtca gcttcgaccc caatatccgc | 780 |
| agcgacctgt ggcaggatcc gcaggaccct cgcgactgtc tcgaccgggc gctggccctc | 840 |
| gccgacgcca taaaactttc ggaagaggag ctggcgttta tcagcggcag cgacgacatc | 900 |
| gtcagcggca ccgcccggct gaacgcccgc ttccagccga cgctactgct ggtgacccag | 960 |
| ggtaaagcgg gggtccaggc cgccctgcgc gggcaggtta gccacttccc tgcccgcccg | 1020 |
| gtggtggccg tcgataccac cggcgccggc gatgcctttg tcgccgggct actcgccggc | 1080 |
| ctcgccgccc acggtatccc ggacaacctc gcagccctgg ctcccgacct cgcgctggcg | 1140 |
| caaacctgcg gcgccctggc caccaccgcc aaaggcgcca tgaccgccct gccctacagg | 1200 |
| gacgatcttc agcgctcgct gtgatcccct ggggccggtt aacggccac tttgctggcg | 1260 |
| acatcacaat tcttaaaccg gtttagcaat ttttattttc accgcgttac cgacatgttt | 1320 |
| accatatcaa ctaaaccggt ttagcaaacg ttagcacact cactgattta cctttggatg | 1380 |
| tcaccaacat gtataaaaaa cggaagttag ccattcttat tgctttgcta accggcaccg | 1440 |
| ccgccgccca tgggcagaca gacctgaaca gcattgaagc gcgtctcgcc gccctggaaa | 1500 |
| aacgcctgca ggacgccgag acccgcgcca gcactgccga agccgcgcc gcctcagcgg | 1560 |
| agcagaaagt tcagcagtta acccagcagc agcagcaaac ccaggccacc acccagcagg | 1620 |
| tggccaggcg caccactcaa ctggaagaaa agccgaacg gcccggcggc tttgagttcc | 1680 |
| acggctatgc gcgttccggg gtgatcatga acgactcggc cgccagtacc aaatccggcg | 1740 |
| cttatatgac ccccgccggg gagaccggcg gcgccattgg tcgcctgggc aaccaggccg | 1800 |

```
acacctatgt ggaaatgaac ctcgaacata aacagaccct ggacaacggg gcgaccaccc   1860
gtttcaaagt gatggtggcc gacggacaga ccacttataa cgactggacg gcaagcagca   1920
gcgatctgaa cgtgcgccag gcgttcgtcg agctgggcaa cctgccgacc ttcgaaggcc   1980
cgttcagagg ctcgaccctg tgggccggga aacgctttga ccgcgacaac ttcgacatcc   2040
actggattga ctcggatgtg gtgttcctcg ccgggaccgg cggcgggatc tacgacgtga   2100
aatggaacga cagcctgcgc agcaacttct cgttatacgg ccgcaacttt ggcgatatcg   2160
ccgacagcag caacagcgtg cagaactata tcgtcagcat gaataacttt gccggcccgg   2220
tgcggatgat ggtcagcggg atgcgggcga agataatga cgaccgccag gacgcgaacg   2280
gcaatctggt gaaaggcgat gccgctaaca ccggggttca tgccctgctg ggcctgcaca   2340
atgagagctt ctatggcctg cgcgacggga ccagcaaaac ggccctgctg tacggccacg   2400
ggctgggcgc cgaggttaaa ggcatcggct ccgacggcgc gctgcgcccg ggggccaata   2460
cctggcgctt cgccagctat ggcaccacgc cgctgagcga tcgctggttt attgccccgg   2520
ccgtgctggc gcagagcagt aaagatcgtt atgtcgatgg cgacagctat cagtgggcca   2580
ccctcaacct gcgtctgatt caggaagtga cgcagaactt cgccctcgcc tgggagggca   2640
gctatcagta catggatctg cagcctgaag gctacaacga tcgccatgcg gtcaatggca   2700
gcttctacaa gctgaccttc gccccgacct tcaaggtggg cagcatcggc gacttcttct   2760
cgcggccgga gatccgcttc tatacatcgt ggatggactg gagcaaaaaa ctggacaact   2820
acgccaacga tgacgcgtta ggcagcaacg gattcaaatc gggcggcgaa tggtcgttcg   2880
gtatgcaaat ggagacctgg ttctgacggc aaccggggcg acagggtaaa taacacataa   2940
atataaggtt cgcggcgcct gccacggctg gcgccgccca cgccatatca tcatgcattt   3000
agagggtact atggattttg aacagatttc ccgctcactg cttccctgc tgggcggcaa    3060
ggaaaatatc gccagcgccg cgcactgcgc cacccgcctg cggctggtgc tggtcgacga   3120
cgcgctcgcc gatcagcagg cgattggcaa aatcgacggg gtgaaaggct gctttcgcaa   3180
tgccggacag atgcagatca tcttcggcac cggggtggtc aataaagtct atgccgcctt   3240
tatccaggcc gcaggcatca gcgaatcgag caaatccgaa gccgccgacc tggcggcgaa   3300
aaagctgaac ccgttccagc gcatcgcccg cctgctgtcc aacatcttcg tgccgattat   3360
tccggccatc gtcgcctccg gcctgctgat gggcctgctg gggatggtga aaacctacgg   3420
ttgggtcgac ccgagcaacg ctctctatat catgctggat atgtgcagtt cggcggcgtt   3480
tatcattctg ccgatcctga tcggctttac cgccgcacgc gaatttggcg gtaaccccta   3540
tctgggcgcg accctcggcg ggatcctcac ccatccggcg ctgaccaacg cctggggcgt   3600
cgccgccggc ttccacacca tgaatttctt cggcatcgaa gtggcgatga tcggctacca   3660
gggcaccgtc ttcccggtgc tgctggcggt gtggtttatg agcatggtcg agaagcggct   3720
gcgccgcgtg atccctgacg cgctggacct gatcctcact ccgttcctga cggtgattat   3780
ctccggcttt atcgccctgc tgctgatcgg cccggccggt cgcgcgctcg gcacggcat   3840
ttcgtttatc ctcagcacgc ttatcagcca tgccggctgg ctggcgggcc tgctgttcgg   3900
cggcctctat tcggtgatcg tcattaccgg tatccatcac agcttccatg ccatcgaggc   3960
cggactgctg ggcaacccat cgattggcgt caacttcctg ctgccgatct gggcgatggc   4020
caacgtcgcc cagggcggcg cctgctttgc ggtgtggttt aaaaccaaag atgccaaaat   4080
aaagccatc accctgccgt cggcgttttc ggcgatgctg gggatcaccg aggcggcaat   4140
cttcgggatt aacctgcgct ttgtgaaacc gtttatcgcc gcgctggtgg gcggtgccgc   4200
```

```
cggcggcgcc tgggtggtgt cgatgcacgt ctacatgacc gcggtgggcc tgacggcgat    4260
cccggggatg gctatcgtgc aggccagctc gctgctgaac tacattatcg gaatggcgat    4320
cgccttcgcc gtggccttcg cgctctctct gacgctgaaa tacaaaacgg acgctgaata    4380
atgtcattac cgtcacgcct gcctgcgatc ctgcaggccg ttatgcaggg ccagccgcag    4440
gcgctggccg acagccatta tccgcaatgg catctggcgc cggtcaacgg actgctgaac    4500
gatcctaacg cttttgcca ggtcgccggg cgttaccacc tgttttatca gtggaacccg    4560
ctcgcccgcg accataccta taagtgctgg ggacactgga gctctgccga tctgctgcac    4620
tggcggcacg aacctatcgc cctgatgccg gatgaagagt atgaccgcaa cggctgctac    4680
tctggcagcg cggtcgagtt cgagggcgcc ctgactctgt gctacaccgg caacgtgaaa    4740
ttccccgacg gcgggcgcac cgcctggcaa tgtctggcga ccgagaatgc cgatggcacc    4800
ttccgcaagc tggggccggt gctgccgctg ccagaaggct ataccggcca tgtgcgcgac    4860
cctaaagtgt ggcggcagga cgggcgctgg tacatggttc ttggggcgca ggatgtgcaa    4920
cagcgcggca aagtgctgct gtttaccgcc agcgacctgc gggagtggcg cctggtgggc    4980
gagattgccg gcacgacgt aaacggcctg gcgaacgccg gctacatgtg ggagtgcccg    5040
gatctctttc cgctggcgga cacccacctg ctgatctgct gcccgcaggg gctggcccgc    5100
gaagcgcagc gctttctcaa tacctatccg gcggtgtgga tggcaggccg cttcgacgcc    5160
gaacgcggga tcttcgacca cggcccgctg cacgagctgg acagcggatt tgagttctac    5220
gcgccgcaga ccatgcaggc cgatgatggc cgccgcctgc tggttggctg gatgggcgtc    5280
cccgacgggg acgagatgca tcagcccacc cgcgcgcagg gctggatcca tcagatgacc    5340
tgcgtgcgtg agctggagtg gcaggctggc actctgtatc agcgtccgct gcgcgagctg    5400
gtcgccctgc gcggggaagc ccagggctgg tgcggacaga ccctgcccct cgccccgatg    5460
gagctggcct ttgacatcgc ccccaacagc acgctgggc tggactttgc cggcgccctg    5520
cagctcaccg tcaatcgcga cggcctgcgt ctgtcgcgtc gcggcctgca gacggcggag    5580
ctgcatcacc gctactggcg cggcgaggcg cgacgcctgc ggatctttat cgaccgctcc    5640
agcgtggaga ttttcatcaa cgatggcgag ggggtgatga gcagccgctt cttcccgggc    5700
tatccggggc agctcatctt cagcggtgcg acgccggtag cattctgccg ctggctgctg    5760
cggccatgca tggtagaata agcgttttgc tttcaggctc ccgggtgctg atgaaaacca    5820
aacgcgtaac tatcaaagat atcgccgaac tggcgggcgt ctccaaagcg accgccagcc    5880
tggtactcaa cggtcgtggt aaagagctgc gcgtggcgca ggagacgcgc gagcgcgtac    5940
tggcgatcgc tcgcgaacag cactatcagc cgagcattca cgcgcgctcg ctgcgcgata    6000
accgcagcca taccattggt ctggtggtgc cggagatcac caactacggg tttgccgttt    6060
tctcccacga gcttgagacg ctctgccggg aagccggcgt gcagctgctt atctcctgca    6120
ccgacgaaaa ccctggccag gagagcgtgg tggtcaataa catgatcgcc cgccaggtcg    6180
acggcctgat tgtcgcccct tgtatgcaca gcgatgccga ctatcagaaa ctcagcgaac    6240
agctgccggt ggtgctgttt gaccgctccc ccagcgacag cgcctgccg ctggtgatga    6300 ccgactcgt cacccaacg gccgagctga tctcccgtat cgcgcctcag catgcggacg    6360
agttctggtt tctcggcggc cagccgcggc tgtcgccgtc gcgcgaccgg ctggcggggt    6420
tcacccaggg cctggcccag gcggggatca cgctgcgccc tgagtgggtg atcaacggca    6480
actaccaccc cagctccggc tatgagatgt tcgcggcgct ctgcgcgcgg ctggggcgtc    6540
cgccgaaggc gctcttcacc gcggcctgcg ggctgctcga agggtgctg cgctatatga    6600
```

```
gccagcatca tctgctggat tccaatattc atctcgccag cttcgacgat cactatctgt      6660
atgattcgct ttccctgcgc attgataccg tgcagcagga taatcgccag ctggcctggc      6720
actgctacga tctgctcagc cagctgatcg acggtcaggc cccggagccg cttcagcgct      6780
acctgcccgc caccctgcag attcgccatc cctgacggcg cggttggcaa ttagcgtttt      6840
cgcctagcgc gcgccgcttg cctcagcgcc agcagcgcgc tggcgagcac ccgccaaggc      6900
cgatcgttac cggccagcgg taagccacca gcaacgaggg caatccacca tccggcgcca      6960
gcatcaccag attccagccc gccagccccg cgttgccgtt cagcgcccgg cttaacatcc      7020
actagtaggg caaactatta actggcgaac tacttactct agcttcccgg caacaattaa      7080
tagactggat ggaggcggat aaagttgcag gaccacttct cgctcggcc cttccggctg       7140 gctggtttat tgctgataaa tctggagccg gtgagcgtgg gtctcgcggt atcattgcag      7200
cactggggcc agatggtaag ccctcccgta tcgtagttat ctacacgacg gggagtcagg      7260
caactatgga tgaacgaaat agacagatcg ctgagatagg tgcctcactg attaagcatt      7320
ggtaactgtc agaccaagtt tactcatata tactttagat tgatttaaaa cttcattttt      7380
aatttaaaag gatctaggtg aagatccttt ttgataatct catgaccaaa atcccttaac      7440
gtgagttttc gttccactga gcgtcagacc ccttaataag atgatcttct tgagatcgtt      7500
ttggtctgcg cgtaatctct tgctctgaaa cgaaaaaac cgccttgcag ggcggttttt       7560
cgaaggttct ctgagctacc aactctttga accgaggtaa ctggcttgga ggagcgcagt      7620
caccaaaact tgtcctttca gtttagcctt aaccggcgca tgacttcaag actaactcct      7680
ctaaatcaat taccagtggc tgctgccagt ggtgcttttg catgtctttc cgggttggac      7740
tcaagacgat agttaccgga taaggcgcag cggtcggact gaacggggg ttcgtgcata       7800 cagtccagct tggagcgaac tgcctacccg gaactgagtg tcaggcgtgg aatgagacaa      7860
acgcggccat aacagcggaa tgacaccggt aaaccgaaag gcaggaacag gagagcgcac      7920
gagggagccg ccaggggaa acgcctggta tctttatagt cctgtcgggt ttcgccacca       7980
ctgatttgag cgtcagattt cgtgatgctt gtcagggggg cggagcctat ggaaaaacgg      8040 cttttgccgcg gccctctcac ttccctgtta agtatcttcc tggcatcttc caggaaatct     8100
ccgccccgtt cgtaagccat ttccgctcgc cgcagtcgaa cgaccgagcg tagcgagtca     8160
gtgagcgagg aagcggaata tatcctgtat cacatattct gctgacgcac cggtgcagcc      8220 tttttctcc tgccacatga agcacttcac tgacaccctc atcagtgcca acatagtaag       8280
ccagtataca ctccgctagc gctgaggtct gcctcgtgaa gaaggtgttg ctgactcata      8340
ccaggcctga atcgccccat catccagcca gaaagtgagg gagccacggt tgatgagagc      8400
tttgttgtag gtggaccagt tggtgatttt gaacttttgc tttgccacgg aacggtctgc      8460
gttgtcggga agatgcgtga tctgatcctt caactcagca aaagttcgat ttattcaaca      8520
aagccacgtt gtgtctcaaa atctctgatg ttacattgca caagataaaa atatatcatc      8580
atgaacaata aaactgtctg cttacataaa cagtaataca aggggtgtta tgagccatat      8640
tcaacgggaa acgtcttgct cgaggccgcg attaaattcc aacatggatg ctgatttata      8700
tgggtataaa tgggctcgcg ataatgtcgg gcaatcaggt gcgacaatct atcgattgta      8760
tgggaagccc gatgcgccag agttgtttct gaaacatggc aaaggtagcg ttgccaatga      8820
tgttacagat gagatggtca gactaaactg gctgacggaa tttatgcctc ttccgaccat      8880
caagcatttt atccgtactc ctgatgatgc atggttactc accactgcga tccccgggaa      8940
aacagcattc caggtattag aagaatatcc tgattcaggt gaaaatattg ttgatgcgct      9000
```

```
ggcagtgttc ctgcgccggt tgcattcgat tcctgtttgt aattgtcctt ttaacagcga    9060
tcgcgtattt cgtctcgctc aggcgcaatc acgaatgaat aacggtttgg ttgatgcgag    9120
tgattttgat gacgagcgta atggctggcc tgttgaacaa gtctggaaag aaatgcataa    9180
gcttttgcca ttctcaccgg attcagtcgt cactcatggt gatttctcac ttgataacct    9240 tattttttgac gagggggaaat taataggttg tattgatgtt ggacgagtcg gaatcgcaga   9300
ccgataccag gatcttgcca tcctatggaa ctgcctcggt gagttttctc cttcattaca    9360
gaaacggctt tttcaaaaat atggtattga taatcctgat atgaataaat tgcagtttca    9420
tttgatgctc gatgagtttt tctaatcaga attggttaat tggttgtaac actggcagag    9480
cattacgctg acttgacggg acggcggctt tgttgaataa atcgaacttt tgctgagttg    9540
aaggatcaga tcacgcatct tcccgacaac gcagaccgtt ccgtggcaaa gcaaaagttc    9600
aaaatcacca actggtccac ctacaacaaa gctctcatca accgtggctc cctcactttc    9660
tggctggatg atgggggcgat tcaggcctgg tatgagtcag caacaccttc ttcacgaggc    9720
agacctcagc gctcaaagat gcaggggtaa aagctaaccg catctttacc gacaaggcat    9780
ccggcagttc aacagatcgg gaaggggctgg atttgctgag gatgaaggtg gaggaaggtg    9840
atgtcattct ggtgaagaag ctcgaccgtc ttggccgcga caccgccgac atgatccaac    9900
tgataaaaga gtttgatgct cagggtgtag cggttcggtt tattgacgac gggatcagta    9960
ccgacggtga tatggggcaa atggtggtca ccatcctgtc ggctgtggca caggctgaac   10020
gccggaggat cctagagcgc acgaatgagg gccgacagga agcaaagctg aaaggaatca   10080
aatttggccg caggcgtacc gtggacagga acgtcgtgct gacgcttcat cagaagggca   10140
ctggtgcaac ggaaattgct catcagctca gtattgcccg ctccacggtt tataaaattc   10200
ttgaagacga aagggcctcg tgatacgcct attttttatag gttaatgtca tgataataat   10260
ggtttcttag acgtcaggtg gcacttttcg gggaaatgtg cgcggaaccc ctatttgttt   10320 attttttctaa atacattcaa atatgtatcc gctcatgaga caataaccct gataaatgct   10380
tcaataatat tgaaaaagga agagtatgag tattcaacat ttccgtgtcg cccttattcc   10440
cttttttgcg gcattttgcc ttcctgtttt tgctcaccca gaaacgctgg tgaaagtaaa   10500
agatgctgaa gatcagttgg gtgcac                                       10526

<210> SEQ ID NO 18
<211> LENGTH: 10707
<212> TYPE: DNA
<213> ORGANISM: Artificial Sequence
<220> FEATURE:
<223> OTHER INFORMATION: pAscrEC

<400> SEQUENCE: 18
cccctgaccg taatagtgaa gggaaaattc gctataaata tcaacaagcc agacgacaac      60
caataaagcc catatcgccc atattcccca aagcaggttg taattacgca ccgggataaa    120
cccagaaaga ggtggggtaa cgcatatcct tctccattcg tcctttttgc agcttaattt    180
ccagattaat tctggccacg ccccataact atcggatggt aagcccttttt gtttagtcct   240 atgaccgtgg caacgtgatg actatcgcat aaattttcac caacacggtg tggaaatgta    300 agtttttattg atgtgggtgc gtctctgcgg tgaagggtat tgcttagcta aaccgattct    360 tctatttttag caaatagtct gactatcgtt gataagagta actttatggc aaacaaaatt    420
tgggtcatgg gcgacgccgt tgtcgatctc atcccggaag atacgaaacg ctatctgaaa    480
tgtcctggcg gtgcgccagc caatgtcgcg gttggcattg ccagactggg gggaaacagc    540
```

```
gcctttgtcg gtcgcgtcgg tgacgatgtt tttggccatt ttctaaaaac ggtgctggaa    600
gaagaaaacg tcgatacccca ctacatggcg tacgacagac accaccgcac atcaaccgtg    660
gtcgtgagcc tcgatgacgc gggtgaacgc accttcacgt ttatggtacg cccgagtgcc    720
gacctgttcc tacaaccgga agatctgccg gtattcaacc ggagagaatg gctgcatctc    780
tgttctatcg cactgtcgca ggaaccgtcg cgcagtaccg cgtttgaggc aatgcgacag    840
attaaagccg cgctggggcg cgtttgcttc gaccccaata tccgtgacga cctctggcaa    900
agcgagcagg aactgcgcga ctgcctgaca caagcgctga tgctggccga tgtggtgaaa    960
ctgtcgtgtg aagagctgac ctttctctgt ccaacatctg atgttgaaga agggatccag   1020
caattcatgc tgcgctaccc cactcggcta ttgctggtga cactgggcag cgaaggtgtc   1080
tggctgcacg atcgccacca gctacaacac tttgctgccc cctcggtgac acctgtcgat   1140
accacgggtg caggggatgc cttcgttgcc ggtttgctgc acggtctggc ggaatatgat   1200
gatttgtcac agccgctgag ctgggatccg attatcgagc aggcgcaacg gtgcggcgca   1260
ctagctacta cggcaaaagg cgcgatgacg gcgcttccct atgcccagca gttgtacaca   1320
ctccccttag ccaaggtcta atcccccct cgtttaatac gattaccgcc cggttttgta    1380
gtcaggatca cagttacaga atcgggtgag tgaaatttct tgctaaccct tctgctggct   1440
tttattttcc tcaagaaaaa ccggtttagc aatttagcta acatgagaa ttccaaaaac    1500
aataaatctc cttcacgacg agaacgaaaa aatgaaacca gccaccttg ctgtgacgat    1560
aggattatta ctctccgccc cgttttatgt ttctgctgcc aacaccgaca gtatcgaaga   1620
ccgcctgaac gcaatggaac aacgcttgca acaggctgaa gcccgcgctc aggccgccga   1680
agccagagcc aatgctgctg aaaagcaaac ccagcagcta gcaacccgca ccacccaaac   1740
cgaacaaaaa acccagcagg tggagcagcg cacaacggcg ctggccaaac agaagtcatt   1800
ctccgatgga ttcgaattcc acggctacgc gcgttccggc ctgtcgatca atgattccgc   1860
caccagtgcc aaaaccgata tcgggccggg catgtcccct gccggtcaga caggcgggca   1920
tattggtcgt ttgggtaatg aagacgacac ctacgtcgag ctcaaactag agcacaaaca   1980
gaagctggat aacggcgcaa ccacccgatt caaggtgatg atggcggacg gtcagcgcag   2040
ctataacgac tggacggcga ccaccagcga tctgaacatc cgcgaagcct tcgtcgagct   2100
gggctcactg ccgactttca ccgatgtctt taaggacact acgctgtggg cgggtaaacg   2160
cttcgatcgc gataacttcg atatccactg gctggatagc gatgtcgtgt tcctcgccgg   2220
tactggcggc gggatctatg acgtgaaatg ggcagatagc gccaagagta acttctcgct   2280
gtatggccgc agcctcggtg aaatcacctc gctggataac gacatcaaaa actacgtctt   2340
taccgccaac aactacgttg ggccattcca gttcatgctg agcggattaa ccgcgaagaa   2400
caatgatgta aaagagaaca ctggcacaag ccgcgataac atcaccgtca ccaataccaa   2460
tgcgggcggc aaaggctatc acgcgatggt ggcttaccac ggcgacagct tctacggctt   2520
acgcgacggg acatcgaaaa ctgcgatcct ctacggccac gggctaggcg gcgaagtgaa   2580
gagtatcggt tccgacggta acctcaccaa cgacgccaac acatggcgct ttgcgaccta   2640
cggcacaaca gcgctgaaca agacctggag cttcgcaccg tccattctgg cgcaaaccag   2700
caaagaccgt tacgtcagcg gcgatagcta cgaatgggtg accttttaatg cgcgcctgat   2760
tcaggaaatc accgaaaact ttgcactggc ctatgaaggc agctatcaat acatgggcct   2820
cgatccgcgc ggttatcgga gcctgaatca ggtgagcggc ggcttctata aactgacctt   2880
cgcgcctaca ttcaaggttg gcgatatcgg caacttcttc agccgtcctg aactacgcgt   2940
```

```
gtttgccagc tacatggact gggataaacg actggataac tactccaacg atgatacgtt   3000
cggctccacc ggctttaaag caggcggcga atggaacttt ggcatccaga tggaaacctg   3060
gttctgatca ttggctagcc ttggcgtcga tgacacgcta atcgacgcca aagaaactgc   3120
atatcctatt gaaaagagg aataacatgg atatcaatgc tactgccgcc gcgctaatcc    3180
cccttctcgg tgggaaagaa aacatcgcca gcgcggccca ctgtgcgacc cgtctacgtc   3240
tggtattgaa tgacgacagc ctggccgaca agaaagcgat cgagaacgtt gacggcgtga   3300
aaggatgctt ccagaacgcc ggacaaatgc agattatttt cggcaccgga ctggttaaca   3360
aagtgtatgc cgagttcatt aaagccgcag gtatcagcga atcaagcaaa tctgaagccg   3420
cctctatcgc ggcgagaaag ctgaatccgc tgcaacgtct ggcgcgtctg ctatcgaaca   3480
tcttcgtccc tataatgcca gcgattatcg cttccggcct gttgatgggg ctgctcggca   3540
tgatcaagac ctacggctgg gtagatgcca acagcgcgat ctttgtgatg ctggatatgt   3600
tcagctccgc tgcctttatt atcctgcctg ttctgatcgg ttttaccgct gcacgggaat   3660
tcggcggcaa cccctatctg ggtgcaacgc tgggcggcat tctgacccat cctgcgctga   3720
ccaacgcttg gggcgtggcg gggggcttcc agaccatgca tttcttcggc atggacattg   3780
ccatgattgg ctatcagggt accgtattcc cagtactgct ggccgtctgg ttcatgagtc   3840
ttgtggaaaa acgcctgcgt aaagtcgtac cggacgcact ggacatcatc gttacgcctt   3900
tcctgacggt catcatctcc ggcttcgtcg cgatgctgct catcggccca gcaggacgcg   3960
cgcttggcga tggtatttct ctcgtcctca gcacgttgat tgctcatgct ggctggttcg   4020
cgggtttact gttcggtggc ctctactccg tcatcgtgat caccggcgtt caccacagct   4080
tccatgcgat tgaagccgga ctactcggca acccgaatat cggcgtcaac ttcctgctgc   4140 caattgggc aatggcgaac gtggcgcagg gcggcgcgtg tctggcggtc tactttaaaa    4200
cgcgtgacgc caaaaccaga gcgattgccg ttccggcggg gctttcctgt ctgctgggta   4260
tcaccgaagc agcgatcttt ggtatcaacc tgcgtttcat taagccgttc ctcgcagcac   4320
tggcgggtgg tgcgctcggt ggcgcatggg tcgtcttcaa tcacgtcaat atgacggcgg   4380
tcgggctgac cggttttccg gggctagcca ttgtgcaagg tggctcgatg cttaactacc   4440
tgattgggat gttgattgca ttcggtgccg cctttgtcat ttccttattg ctgaaataca   4500
aaacggatag cgaataatga aggaagtcca cttagtaaaa cgcatggcgc acgccctgat   4560
gtcaggtcac tcacggaaac aggaagaccc atatcgcccg gaatggcatc tgtcaccgtg   4620
tgtgggtctg cttaacgatc cgaacggatt tattcatcac aacggcgtt accatctgtt    4680 ttatcagtgg aatcctttgg cctgtgccca cggagcaaaa ttctggggc actggagttc    4740 cgccgatctg gtgaactgga agcatgaacc cgtcgcgctg gtgccgagcg aaagctatga   4800
aagccacggc tgctactccg gttctgccgt cgtagatcac ggtgcgatca cgctgattta   4860
cacgggtaac gtcaaatacg acgatggctc acgcaccgcg tttcagtgtc tcgcccgcga   4920
aaatcctaac ggtgaatacg acaagctggg agcggttctg acgctcccag acggctacac   4980
tggccacgtt cgcgatccga aagtgtgcg tcatggtgac cactggtaca tggtgctcgg    5040
cgcacaggat ctcgatcttc agggggaaggt cgtgctctat cgttctgccg atctgctggc   5100
gtgggaaaag atcgccgaga tcgccggctc tcgtttgggc gggctcggtg attttggtta   5160
tatgtgggag tgtccagact tgttcccgct ggatggcgaa gacatactga tttgctgccc   5220
acaaggcgtt cccgctgaag atgaacgcta cctgaatacc tttcaggcgg gctatttcat   5280
tggctcactc gactacgaaa acggcgatta ctcgcatcag ggtttccatg aactggatct   5340
```

```
cggctttgag ttttacgccc cacaaaccac gctgagtgaa gacgggcgac gcctgctgtt    5400
tggctggatg tcgattcctg acgacaatga attttttgaa ccgacgatcg agcacggctg    5460
gattcatact atgacctgcg cgcgtgaact cacgctgcat gacgatcgcg tttatcaacg    5520
tcctgcgcgc gaattacaac agttgcgcag acagcattac acctggcgtg gtgcagcaga    5580
ctacgcgtcg ccgctaccca ttagtagcgc agaagtgctc atcaccgttc aggggggaatt    5640 ccagctcaat cttgcctccc agcttgttct ctgttgggac ggtgaacgcg taacgataag    5700
ccgacgcaac cgacgcacag gcgaacctga acatcgctac tggcgcggcg acctgcgtca    5760
attacagata ttgtgcgatc gctccagcgt tgaaatttt atcaacgatg gcgaggccgt     5820
gatgtctgca cgaactttcc cggaaagcga ggcgaccatg acgttcagcg gctctgggca    5880
attaacgcta caacactggc tgttagcgcc atgcgtgata gaataacttt ccttttttct    5940
gatagcagac ctcgcggtga aaccgactaa acgcataaca atcagtgaca tcgccgcgct    6000
ggccggtgta tcaaaatcta ccgccagcct ggtgctgaac ggccgcagca aagagttccg    6060
cgtttctgat gaaacgcgcg atcgcatttt agccgtcgca cacgagcagc gttatcagcc    6120
cagtattcac gcacgttcac tgcgttcctc acgcagtaac acgctggggc tggtggtgcc    6180
agaaatgacc aactacggct tgccgtgat ttcccgcgaa ctggagatgc ggtgccgcga     6240
agctgggcta cagttgctaa ttgcctgtac cgatgaaaat gccagtcagg agatgatggc    6300
ggtcaacagt ctggtacagc gccaggtcga tggcctgatt gtcgcttcca gcctgctgag    6360
tgatatcgag tatcagaaaa ttaatcagca gctgcccgtc gtgcaatttg accggattat    6420
tggtgattcc acactgccga tggtcatttc gaagcggta gaatccacag cagaaatggt     6480
cgagcgtatc gcccgccagc atcgtgatga attttatttc cttggcggcc agccgcgaat    6540
ttccccgact cgccaccgtc tggaaggctt tcagcttggg ttgacgcgtg ccggtatcga    6600
gtgccagccg gagtggattc ttcatggcaa ctaccacccc agcgcaggtt atgaaatgtt    6660
tgctcaactg tgtgcgacgc tgggtcgccc gccaaaagca ctgtttgttg ccgcctgtgg    6720
cctgatggaa ggcgtgctgc gttatatgaa ccagcataac ctgatggaaa gcggcatccg    6780
tctgtgctgc tttgacgatc actatctgtt tgattgttta ccgctgaaga tcgataccgt    6840
ggcgcaggat tgtgaaaatc tggcacgcaa cagctttgaa atgattacga gtttgattgc    6900
acaacagccg cttgaagaag atcggcgcta tatcccgacg cggattcact ggcgtcatcc    6960
tgactcgcgg gcatgactcg cgacatagcc caacacactt caccagcagg tagaacgtaa    7020
aaagggaacg cggttagcgt cgcttcttag agcatcgcac cacattccct tttgaatcga    7080
tcagccgtta cttagcggcg gcagattccg cgccaaccag acccacccttg aggtagcccg    7140 ctttacgcag tgaatccatc acgctcatga tggtttcata atcgacgctt ttatctgcct    7200
gactagtagg gcaaactatt aactggcgaa ctacttactc tagcttcccg gcaacaatta    7260
atagactgga tggaggcgga taaagttgca ggaccacttc tgcgctcggc ccttccggct    7320
ggctggttta ttgctgataa atctggagcc ggtgagcgtg ggtctcgcgg tatcattgca    7380
gcactggggc cagatggtaa gccctcccgt atcgtagtta tctacacgac ggggagtcag    7440
gcaactatgg atgaacgaaa tagacagatc gctgagatag gtgcctcact gattaagcat    7500
tggtaactgt cagaccaagt ttactcatat atactttaga ttgatttaaa acttcatttt    7560
taatttaaaa ggatctaggt gaagatcctt tttgataatc tcatgaccaa aatcccttaa    7620
cgtgagtttt cgttccactg agcgtcagac cccttaataa gatgatcttc ttgagatcgt    7680
tttggtctgc gcgtaatctc ttgctctgaa aacgaaaaaa ccgccttgca gggcggtttt    7740
```

-continued

```
tcgaaggttc tctgagctac caactctttg aaccgaggta actggcttgg aggagcgcag   7800
tcaccaaaac ttgtcctttc agtttagcct taaccggcgc atgacttcaa gactaactcc   7860
tctaaatcaa ttaccagtgg ctgctgccag tggtgctttt gcatgtcttt ccgggttgga   7920
ctcaagacga tagttaccgg ataaggcgca gcggtcggac tgaacggggg gttcgtgcat   7980
acagtccagc ttggagcgaa ctgcctaccc ggaactgagt gtcaggcgtg aatgagaca   8040 aacgcggcca taacagcgga atgacaccgg taaaccgaaa ggcaggaaca ggagagcgca   8100
cgagggagcc gccaggggga aacgcctggt atctttatag tcctgtcggg tttcgccacc   8160
actgatttga gcgtcagatt tcgtgatgct tgtcaggggg gcggagccta tggaaaaacg   8220
gctttgccgc ggccctctca cttccctgtt aagtatcttc ctggcatctt ccaggaaatc   8280
tccgccccgt tcgtaagcca tttccgctcg ccgcagtcga acgaccgagc gtagcgagtc   8340
agtgagcgag gaagcggaat atatcctgta tcacatattc tgctgacgca ccggtgcagc   8400
cttttttctc ctgccacatg aagcacttca ctgacaccct catcagtgcc aacatagtaa   8460
gccagtatac actccgctag cgctgaggtc tgcctcgtga agaaggtgtt gctgactcat   8520
accaggcctg aatcgcccca tcatccagcc agaaagtgag ggagccacgg ttgatgagag   8580
ctttgttgta ggtggaccag ttggtgattt tgaacttttg ctttgccacg aacggtctg   8640 cgttgtcggg aagatgcgtg atctgatcct tcaactcagc aaaagttcga tttattcaac   8700
aaagccacgt tgtgtctcaa atctctgat gttacattgc acaagataaa aatatatcat   8760
catgaacaat aaaactgtct gcttacataa acagtaatac aagggtgtt atgagccata   8820 ttcaacggga aacgtcttgc tcgaggccgc gattaaattc aacatggat gctgatttat   8880 atgggtataa atgggctcgc gataatgtcg ggcaatcagg tgcgacaatc tatcgattgt   8940
atgggaagcc cgatgcgcca gagttgtttc tgaaacatgg caaaggtagc gttgccaatg   9000
atgttacaga tgagatggtc agactaaact ggctgacgga atttatgcct cttccgacca   9060
tcaagcattt tatccgtact cctgatgatg catggttact caccactgcg atccccggga   9120
aaacagcatt ccaggtatta gaagaatatc ctgattcagg tgaaaatatt gttgatgcgc   9180
tggcagtgtt cctgcgccgg ttgcattcga ttcctgtttg taattgtcct tttaacagcg   9240
atcgcgtatt tcgtctcgct caggcgcaat cacgaatgaa taacggtttg gttgatgcga   9300
gtgattttga tgacgagcgt aatggctggc ctgttgaaca agtctggaaa gaaatgcata   9360
agcttttgcc attctcaccg gattcagtcg tcactcatgg tgatttctca cttgataacc   9420
ttatttttga cgaggggaaa ttaataggtt gtattgatgt tggacgagtc ggaatcgcag   9480
accgatacca ggatcttgcc atcctatgga actgcctcgg tgagttttct ccttcattac   9540
agaaacggct ttttcaaaaa tatggtattg ataatcctga tatgaataaa ttgcagtttc   9600
atttgatgct cgatgagttt ttctaatcag aattggttaa ttggttgtaa cactggcaga   9660
gcattacgct gacttgacgg gacggcggct ttgttgaata atcgaacttt tgctgagtt   9720 gaaggatcag atcacgcatc ttcccgacaa cgcagaccgt tccgtggcaa agcaaaagtt   9780
caaaatcacc aactggtcca cctacaacaa agctctcatc aaccgtggct ccctcacttt   9840
ctggctggat gatggggcga ttcaggcctg gtatgagtca gcaacacctt cttcacgagg   9900
cagacctcag cgctcaaaga tgcagggta aagctaacc gcatctttac cgacaaggca   9960
tccggcagtt caacagatcg ggaagggctg gatttgctga ggatgaaggt ggaggaaggt  10020
gatgtcattc tggtgaagaa gctcgaccgt cttggccgcg acaccgccga catgatccaa  10080
ctgataaaag agtttgatgc tcagggtgta gcggttcggt ttattgacga cgggatcagt  10140
```

-continued

```
accgacggtg atatggggca aatggtggtc accatcctgt cggctgtggc acaggctgaa    10200
cgccggagga tcctagagcg cacgaatgag ggccgacagg aagcaaagct gaaaggaatc    10260
aaatttggcc gcaggcgtac cgtggacagg aacgtcgtgc tgacgcttca tcagaagggc    10320
actggtgcaa cggaaattgc tcatcagctc agtattgccc gctccacggt ttataaaatt    10380
cttgaagacg aaagggcctc gtgatacgcc tattttata ggttaatgtc atgataataa     10440
tggtttctta gacgtcaggt ggcacttttc ggggaaatgt gcgcggaacc cctatttgtt    10500
tatttttcta aatacattca aatatgtatc cgctcatgag acaataaccc tgataaatgc    10560
ttcaataata ttgaaaaagg aagagtatga gtattcaaca tttccgtgtc gcccttattc    10620
ccttttttgc ggcattttgc cttcctgttt ttgctcaccc agaaacgctg gtgaaagtaa    10680
aagatgctga agatcagttg ggtgcac                                        10707

<210> SEQ ID NO 19
<211> LENGTH: 1728
<212> TYPE: DNA
<213> ORGANISM: Escherichia coli K-12 W3110
<220> FEATURE:
<221> NAME/KEY: gene
<222> LOCATION: (1)..(1728)
<223> OTHER INFORMATION: ptsI

<400> SEQUENCE: 19
atgatttcag gcattttagc atccccgggt atcgctttcg gtaaagctct gcttctgaaa      60
gaagacgaaa ttgtcattga ccggaaaaaa atttctgccg accaggttga tcaggaagtt    120
gaacgttttc tgagcggtcg tgccaaggca tcagcccagc tggaaacgat caaaacgaaa    180
gctggtgaaa cgttcggtga agaaaaagaa gccatctttg aagggcatat tatgctgctc    240
gaagatgagg agctggagca ggaaatcata gccctgatta agataagca catgacagct    300 gacgcagctg ctcatgaagt tatcgaaggt caggcttctg ccctggaaga gctggatgat    360
gaatacctga agaacgtgc ggctgacgta cgtgatatcg gtaagcgcct gctgcgcaac    420
atcctgggcc tgaagattat cgacctgagc gccattcagg atgaagtcat tctggttgcc    480
gctgacctga cgccgtccga aaccgcacag ctgaacctga gaaggtgct gggtttcatc    540 accgacgcgg gtggccgtac ttcccacacc tctatcatgg cgcgttctct ggaactacct    600
gctatcgtgg gtaccggtag cgtcaccgct caggtgaaaa atgacgacta tctgattctg    660
gatgccgtaa ataatcaggt ttacgtcaat ccaaccaacg aagttattga taaaatgcgc    720
gctgttcagg agcaagtggc ttctgaaaaa gcagagcttg ctaaactgaa agatctgcca    780
gctattacgc tggacggtca ccaggtagaa gtatgcgcta acattggtac ggttcgtgac    840
gttgaaggtg cagagcgtaa cggcgctgaa ggcgttggtc tgtatcgtac tgagttcctg    900
ttcatggacc gcgacgcact gcccactgaa gaagaacagt ttgctgctta caagcagtg    960 gctgaagcgt gtggctcgca agcggttatc gttcgtacca tggacatcgg cggcgacaaa    1020
gagctgccat acatgaactt cccgaaagaa gagaacccgt tcctcggctg gcgcgctatc    1080
cgtatcgcga tggatcgtag agatcctg cgcgatcagc tccgcgctat cctgcgtgcc    1140
tcggctttcg gtaaattgcg cattatgttc ccgatgatca tctctgttga agaagtgcgt    1200
```

-continued

| | |
|---|---|
| gcactgcgca aagagatcga atctacaaa caggaactgc gcgacgaagg taaagcgttt | 1260 |
| gacgagtcaa ttgaaatcgg cgtaatggtg gaaacaccgg ctgccgcaac aattgcacgt | 1320 |
| catttagcca aagaagttga tttctttagt atcggcacca atgatttaac gcagtacact | 1380 |
| ctggcagttg accgtggtaa tgatatgatt tcacaccttt accagccaat gtcaccgtcc | 1440 |
| gtgctgaact tgatcaagca agttattgat gcttctcatg ctgaaggcaa atggactggc | 1500 |
| atgtgtggtg agcttgctgg cgatgaacgt gctacacttc tgttgctggg gatgggtctg | 1560 |
| gacgaattct ctatgagcgc catttctatc ccgcgcatta agaagattat ccgtaacacg | 1620 |
| aacttcgaag atgcgaaggt gttagcagag caggctcttg ctcaaccgac aacggacgag | 1680 |
| ttaatgacgc tggttaacaa gttcattgaa gaaaaaacaa tctgctaa | 1728 |

<210> SEQ ID NO 20
<211> LENGTH: 258
<212> TYPE: DNA
<213> ORGANISM: Escherichia coli K-12 W3110
<220> FEATURE:
<221> NAME/KEY: gene
<222> LOCATION: (1)..(258)
<223> OTHER INFORMATION: ptsH

<400> SEQUENCE: 20

| | |
|---|---|
| atgttccagc aagaagttac cattaccgct ccgaacggtc tgcacacccg ccctgctgcc | 60 |
| cagtttgtaa aagaagctaa gggcttcact tctgaaatta ctgtgacttc caacggcaaa | 120 |
| agcgccagcg cgaaaagcct gtttaaactg cagactctgg gcctgactca aggtaccgtt | 180 |
| gtgactatct ccgcagaagg cgaagacgag cagaaagcgg ttgaacatct ggttaaactg | 240 |
| atggcggaac tcgagtaa | 258 |

<210> SEQ ID NO 21
<211> LENGTH: 510
<212> TYPE: DNA
<213> ORGANISM: Escherichia coli K-12 W3110
<220> FEATURE:
<221> NAME/KEY: gene
<222> LOCATION: (1)..(510)
<223> OTHER INFORMATION: crr

<400> SEQUENCE: 21

| | |
|---|---|
| atgggtttgt tcgataaact gaaatctctg gtttccgacg acaagaagga taccggaact | 60 |
| attgagatca ttgctccgct ctctggcgag atcgtcaata tcgaagacgt gccggatgtc | 120 |
| gtttttgcgg aaaaaatcgt tggtgatggt attgctatca aaccaacggg taacaaaatg | 180 |
| gtcgcgccag tagacggcac cattggtaaa atctttgaaa ccaaccacgc attctctatc | 240 |
| gaatctgata gcggcgttga actgttcgtc cacttcggta tcgacaccgt tgaactgaaa | 300 |
| ggcgaaggct tcaagcgtat tgctgaagaa ggtcagcgcg tgaaagttgg cgatactgtc | 360 |
| attgaatttg atctgccgct gctggaagag aaagccaagt ctaccctgac tccggttgtt | 420 |
| atctccaaca tggacgaaat caaagaactg atcaaactgt ccggtagcgt aaccgtgggt | 480 |
| gaaaccccgg ttatccgcat caagaagtaa | 510 |

MICROORGANISM WHICH PRODUCES L-AMINO ACID AND METHOD FOR PRODUCING L-AMINO ACID USING THE SAME

REFERENCE TO SEQUENCE LIST SUBMITTED ELECTRONICALLY VIA EFS-WEB

The content of the electronically submitted sequence listing (Name: 2511_0150001_SequenceListing.ascii.txt; Size: 69,842 bytes; and Date of Creation: Mar. 18, 2013) is incorporated by reference in its entirety.

BACKGROUND OF THE INVENTION

1. Field of the Invention

The present invention relates to a microorganism belonging to the genus Escherichia sp. having a sucrose assimilability and an L-amino acid producing ability, which is obtained by introducing a gene encoding a sucrose assimilative microorganism-derived sucrose metabolic enzyme to a sucrose non-assimilative microorganism belonging to the genus Escherichia sp. having an L-amino acid producing ability and a sucrose PTS (phosphoenolpyruvate dependent sucrose phosphotransferase system) activity, and a method for producing an L-amino acid using the same.

2. Description of the Related Art

Due to the growing demand for bio-fuel production and crop failures caused by unusual climate, the price of starch sugar mainly used in industrial fermentation has rapidly increased. Alternatively, the use of sucrose or molasses containing a high concentration of sucrose, cheaper than starch sugar, as a carbon source in industrial fermentation, is advantageous to ensure the cost competitiveness.

Approximately 50% of wild-type naturally occurring E. coli is able to metabolize sucrose, but E. coli K12 strain, B strain, C strain or the like usually used in industrial fermentation, have no ability to assimilate sucrose (Mol. Microbiol, (1998) 2:1-8, Can. J. Microbiol. (1999) 45:418-422). Therefore, one of the most important challenges in the fermentation industry is the identification of genes involved in sucrose assimilation, the establishment of enhanced sucrose assimilation-related genes by improvement, and the application of the genes to the sucrose non-assimilative, industrial E. coli strains for the production of desired metabolites.

To impart a sucrose-assimilability to industrial E. coli strains, methods of introducing genes or gene cluster involved in sucrose assimilation, derived from a microorganism having a sucrose-assimilability have been generally used. For example, a method of imparting sucrose-assimilability to E. coli K12 by transformation with the scr regulon that is present in the species Salmonella belonging to the family Enterobacteriaceae (J. Bacteriol. (1982) 151:68-76, Mol. Microbiol. (1998) 2:1-8, J. Bacteriol, (1991) 173:7464-7470, U.S. Pat. No. 7,179,623), Klebsiella pneumoniae (J. Gen. Microbiol. (1988) 134:1635-1644), and Erwinia amylovora (J. Bacteriol. (2000) 182:5351-5358) has been well known in the art. Introduction of the csc regulon derived from non-K12 E. coli or pathogenic E. coli having the sucrose-assimilability (Appl. Environ. Microbiol. (1992) 58:2081-2088, U.S. Pat. No. 6,960,455), introduction of gene cluster involved in sucrose assimilation that is present in conjugative plasmid scr53 isolated from E. coli AB1281 (U.S. Pat. No. 4,806,480), and introduction of scr regulon and sac operon derived from Gram-positive microorganism, Streptococcus mutans (J. Bacterial, (1989) 171:263-271) and Bacillus subtilis (J. Bacteriol, (1989) 171:1519-1523) are also known. U.S. Pat. No. 7,179,623 discloses a method of producing lysine, isoleucine and valine using E. coli K12 that is prepared by introducing an E. coli VKPM B-7915-derived scr regulon thereto.

However, there is still a need of an industrial microorganism having an efficient sucrose utilization system and a fermentation method using the same. Therefore, the present inventors found that an L-amino acid can be produced from sucrose at a high yield using an L-amino acid-producing microorganism belonging to the genus Escherichia sp., which is prepared by introducing a gene cluster involved in sucrose assimilation, derived from a sucrose assimilative Klebsiella pneumoniae, thereby completing the present invention.

SUMMARY OF THE INVENTION

An object of the present invention is to provide a microorganism belonging to the genus Escherichia sp. having sucrose assimilability and an L-amino acid producing ability, which is prepared by imparting sucrose assimilability to a sucrose non-assimilative microorganism belonging to the genus Escherichia sp. having an L-amino acid producing ability.

Another object of the present invention is to provide a method for producing an L-amino acid from sucrose using the microorganism belonging to the genus Escherichia sp. having sucrose assimilability and an L-amino acid producing ability.

BRIEF DESCRIPTION OF THE DRAWINGS

FIG. 1 shows the construction of a recombinant plasmid pAscrKP containing Klebsiella pneumoniae (ATCC700721)-derived scrKYABR according to one specific embodiment of the present invention.

DETAILED DESCRIPTION OF THE PREFERRED EMBODIMENTS

In order to achieve the above objects, the present invention provides a microorganism belonging to the genus Escherichia sp. having a sucrose assimilability and an L-amino acid producing ability, which is obtained by introducing a gene encoding a sucrose assimilative microorganism-derived sucrose metabolic enzyme to a sucrose non-assimilative microorganism belonging to the genus Escherichia sp. having an L-amino acid producing ability and a sucrose PTS (phosphoenolpyruvate dependent sucrose phosphotransferase system) activity.

As used herein, the term "sucrose non-assimilative microorganism" means a microorganism that cannot utilize sucrose as a carbon source, and the term "microorganism having sucrose assimilability and an L-amino acid producing ability" means a microorganism that can metabolize sucrose as a carbon source so as to produce an L-amino acid.

As used herein, the term "sucrose metabolic enzyme" means an enzyme required for utilization of sucrose as a carbon source, and it includes fructokinase, sucrose porin, sucrose PTS permease, sucrose hydrolase, invertase or the like, but is not limited thereto.

In the present invention, the "sucrose metabolic enzyme" is also called "Scr-PTS enzyme".

A metabolic system utilizing sucrose as a carbon source can be largely divided into PTS (phosphoenolpyruvate dependent sucrose phosphotransferase)-based sucrose metabolic system (Scr-PTS system) and non-PTS-based sucrose metabolic system (Scr-non PTS system) according to a phosphate source for phosphorylation of influent sucrose in a cell. Most microorganisms capable of utilizing sucrose have the Scr-PTS system.

A representative example of the PTS-based Scr-PTS system using phosphoenolpyruvate (PEP) as a phosphate source for phosphorylation of sucrose includes a conjugative plasmid pUR400 of Gram-negative *Salmonella typhimurium*, a scr regulon present on the chromosome of *Klebsiella pneumoniae* or the like. The scr regulon is composed of 5 genes, scrK (fructokinase), scrY (sucrose porin), scrA (sucrose-specific EIIBC component), scrB (sucrose-6-phosphate hydrolase) and scrR (LacI-related sucrose-specific repressor), and two operons, scrK and scrYAB are negatively controlled by the ScrR repressor (Mol, Microbiol. (1993) 9:195-209). According to a mechanism of the scr regulon, external sucrose is transported into a periplasmic space through an outer membrane protein (OMP), ScrY. The transported sucrose is transported into a cell in the form of sucrose-6-phosphate through a sucrose PTS cycle including ScrA. Sucrose-6-phosphate is then hydrolyzed to glucose-6-phosphate and fructose which are metabolized by ScrB, and fructose is converted into fructose-6-phosphate by an ATP-dependent ScrK, and the resulting fructose-6-phosphate is metabolized via glycolysis, together with glucose-6-phosphate (J. Biotechnol, (2001) 92:133-158), The sucrose PTS cycle, which functions to convert sucrose into sucrose-6-phosphate and then transports it into the cell, is composed of Enzyme I (EI), histidine protein (HPr), glucose-specific enzyme IIA (EIIAcrr$^{Glc}$), and sucrose-specific enzyme IIBC (EIIBC$^{scr}$) (J. Biotechnol. (2001) 92:133-158/J. Biotechnol. (2004) 110:181-199).

The Scr-PTS system of a Gram-positive microorganism is exemplified by the scr regulon of *Streptococcus mutans*, which is composed of scrK, scrA, scrB, and scrR genes (J. Bacteriol, (2003) 185:5791-5799).

The Scr-non PTS system, which requires no PTS for uptake of sucrose into the cell, is exemplified by the well known csc regulon. The csc regulon is mainly derived from a sucrose-assimilative *E. coli*, and exemplified by csc regulon from the wild type *E. coli* EC3132 (Mol. Gen. Genet. (1992) 235:22-32, U.S. Pat. No. 6,960,455), csc regulon from *E. coli* KO11 (Biotechnol. Lett. (2004) 26:689-693), csc regulon from the pathogenic E. coli O157:H7 (J. Bacteriol. (2002) 184:5307-5316), csc regulon from ATCC13281 (Appl. Microbiol. Biotechnol. (2007) 74:1031-1040) or the like. The csc regulon consists of cscB (proton symport-type sucrose permease), cscK (fructokinase), cscA (sucrose hydrolase), and cscR (LacI-related sucrose-specific repressor), and two operons, cscKB and cscA are negatively controlled by CscR (J. Bacteriol. (2002) 184: 5307-5316).

The Scr-non PTS system is disadvantageous in that it is not efficient for uptake of a low level of sucrose. It was reported that *E. coli* introduced with the csc regulon has a doubling time of 20 hrs in a medium containing sucrose of 0.2% or less (J. Bacteriol. (2002) 184:5307-5316). Unlike the Scr-non PTS system, the Scr-PTS system allows efficient uptake of even a low level of sucrose into the cell, because ScrA as a sucrose PTS permease functions to convert sucrose into sucrose-6-phosphate using a free phosphate produced by conversion of phosphoenolpyruvate (PEP) to pyruvate via the sucrose PTS cycle composed of Enzyme I, histidine protein, and glucose-specific enzyme IIA, while it transports sucrose from the periplasm into the cell. That is, while the uptake of external sucrose by CscB of the Scr-non PTS system is driven by a hydrogen gradient, the Scr-PTS system requires PEP used as an energy source for the uptake of sucrose into the cell, and thus allows efficient uptake of even a low level of sucrose. The CscB of the Scr-non PTS system, which transports the external sucrose into the cell by a hydrogen gradient, has a Km value for sucrose of 1.0 mM (Biochem. BiophysRes. Commun. (1995) 208:1116-1123). In contrast, ScrA has a Km value of 10 μm (J. Bacteriol (1982) 151:68-76), which is 100 times lower than that of CscB. In the Scr-PTS system, the ScrY protein is also involved in efficient uptake of a low level of sucrose, in addition to ScrA. Reportedly, ScrY is a sucrose porin that functions to transport external sucrose into the periplasm, and abnormal expression of the sucrose porin greatly reduces the transport of sucrose (J. Bacteriol. (1991) 173:449-456). That is, in the Scr-PTS system, ScrY transports external sucrose into the periplasm, and ScrA rapidly transports the periplasmic sucrose into the cell via the PTS system, thereby efficiently utilizing even a low level of sucrose.

In a specific embodiment of the present invention, the gene encoding a sucrose assimilative microorganism-derived sucrose metabolic enzyme is a gene derived from a microorganism having a sucrose-assimilating ability, and preferably a gene derived from a microorganism having a PTS-based Scr-PTS system.

In a specific embodiment of the present invention, the gene encoding a sucrose assimilative microorganism-derived sucrose metabolic enzyme refers to a gene derived from a sucrose assimilative microorganism that belongs to the genus *Klebsiella* or *Erwinia*, and more preferably a gene derived from *Klebsiella pneumoniae* ATCC700721 or *Erwinia carotovora* ATCCBAA-672.

In a specific embodiment of the present invention, the gene encoding a sucrose assimilative microorganism-derived sucrose metabolic enzyme may be combinations of the genes encoding fructokinase, sucrose porin, sucrose PTS permease, sucrose hydrolase, and sucrose transcriptional regulator, which are derived from *Klebsiella pneumoniae*.

In a specific embodiment of the present invention, the genes encoding the sucrose assimilative microorganism-derived fructokinase, sucrose porin, sucrose PTS permease, sucrose hydrolase, and sucrose transcriptional regulator may be scrK of SEQ ID NO. 6, scrY of SEQ ID NO. 7, scrA of SEQ ID NO. 8, scrB of SEQ ID NO. 9, and scrR of SEQ ID NO. 10, respectively.

In a specific embodiment of the present invention, the sucrose non-assimilative microorganism belonging to the genus *Escherichia* sp. should have an activity of a sucrose PTS cycle that is composed of Enzyme I (EI), histidine protein (HPr), and glucose-specific enzyme IIA (EIIAcrr$^{Glc}$), excluding ScrA. Preferably, normal expression of the Enzyme I-encoding gene (ptsI, SEQ ID NO. 19), the histidine protein-encoding gene (ptsH, SEQ ID NO. 20), and the glucose-specific enzyme IIA-encoding gene (crr, SEQ ID NO. 21) should occur in the sucrose *Escherichia* sp. microorganism.

For the preparation of the microorganism belonging to the genus *Escherichia* sp. having a sucrose assimilability and an L-amino acid producing ability according to the present invention, introduction of the genes encoding the sucrose assimilative microorganism-derived sucrose porin, sucrose PTS permease, sucrose hydrolase, fructokinase, and sucrose transcriptional regulator into the sucrose non-assimilative microorganism belonging to the genus *Escherichia* sp. may be performed by the method well known in the art.

In a specific embodiment of the present invention, sequences encoding the sucrose porin, the sucrose PTS permease, the sucrose hydrolase, the fructokinase, and the sucrose transcriptional regulator are introduced into a vector to construct a recombinant vector, and the sucrose non-assimilative microorganism belonging to the genus *Escherichia* sp. having an L-amino acid producing ability is transformed with the constructed recombinant vector so as to prepare a microorganism belonging to the genus *Escherichia* sp. having a sucrose assimilability and an L-amino acid producing ability.

The vector used for the preparation of the microorganism belonging to the genus *Escherichia* sp. of the present invention is not particularly limited, and any known expression vectors may be used. Preferably, pACYC177, pACYC184, pCL, pECCG117, pUC19, pBR322, or pMW118 may be used.

As used herein, the term "transformation" means a method in which a gene is introduced into a host cell to be expressed in the host cell. The transformed gene, if it can be expressed in the host cell, may be inserted in the chromosome of the host cell or may exist independent of the chromosome. In addition, the transformed gene is defined as a polynucleotide capable of encoding a polypeptide, and includes DNA and RNA. The transformed gene may be in a suitable form that can be introduced into the host cell and expressed therein. For example, the transformed gene may be introduced into the host cell in the type of expression cassette which is a polynucleotide expressome including whole elements for expressing the gene by itself. Typically, the expression cassette includes a promoter, a transcription termination signal, a ribosome binding site and a translation termination signal, which are operably linked to the transformed gene. The expression cassette may be in the type of the expression vector capable of self-replication. The transformed gene also may be introduced into the host cell by itself or in the type of polynucleotide expressome so as to be operably linked to the sequence required for expression in the host cell.

In a specific embodiment of the present invention, the sucrose non-assimilative microorganism belonging to the genus *Escherichia* sp. having an L-amino acid producing ability may be transformed with a recombinant vector harboring a gene encoding a *Klebsiella pneumoniae*-derived Scr-PTS enzyme in order to acquire a sucrose assimilability.

In a specific embodiment of the present invention, the sucrose non-assimilative microorganism belonging to the genus *Escherichia* sp. having an L-amino acid producing ability may be transformed with a recombinant plasmid including a sequence of SEQ ID NO. 17 in order to acquire a sucrose assimilability. Specifically, the recombinant plasmid including a sequence of SEQ ID NO. 17 includes *Klebsiella pneumoniae* (ATCC700721)-derived scrKYABR, namely, the fructokinase-encoding scrK of SEQ ID NO. 6, the sucrose porin-encoding scrY of SEQ ID NO. 7, the sucrose PTS permease-encoding scrA of SEQ ID NO. 8, the sucrose hydrolase-encoding scrB of SEQ ID NO. 9, and the sucrose transcriptional regulator-encoding scrR of SEQ ID NO. 10.

The microorganism belonging to the genus *Escherichia* sp. having a sucrose assimilability and an L-amino acid producing ability according to the present invention is a microorganism belonging to the genus *Escherichia* sp. that is able to produce L-amino acid, retains the activities of sucrose porin, sucrose PTS permease, sucrose hydrolase, fructokinase, and sucrose transcriptional regulator, and maintains a sucrose PTS activity at the same time, and it may be preferably *Escherichia coli*.

In a specific embodiment of the present invention, the L-amino acid may be L-threonine, O-succinyl-homoserine, O-acetyl-homoserine, L-methionine, L-lysine, L-homoserine, L-isoleucine, L-valine, or L-tryptophan.

In a specific embodiment of the present invention, the L-amino acid may be L-threonine.

In a specific embodiment of the present invention, the microorganism belonging to the genus *Escherichia* sp. having a sucrose assimilability and an L-amino acid producing ability may be *Escherichia coli* CA03-0207 (KCCM 10993) that is obtained by transforming *Escherichia coli* ABA5G having an L-threonine-producing ability with a vector having the sequence of SEQ ID NO. 17 including the scrKYABR gene cluster.

Further, the present invention provides a method for producing an L-amino acid, comprising the steps of culturing the microorganism belonging to the genus *Escherichia* sp. having a sucrose assimilability and an L-amino acid producing ability in a medium containing sucrose as a carbon source; and recovering an L-amino acid from the culture medium.

In a specific embodiment of the present invention, the L-amino acid may be L-threonine, O-succinyl-homoserine, O-acetyl-homoserine, L-methionine, L-lysine, L-homoserine, L-isoleucine, L-valine, or L-tryptophan.

In a specific embodiment of the present invention, the L-amino acid may be L-threonine.

The method for producing an L-amino acid according to the present invention includes the step of culturing the microorganism belonging to the genus *Escherichia* sp. having a sucrose assimilability and an L-amino acid producing ability.

In a specific embodiment of the present invention, the step of culturing the microorganism belonging to the genus *Escherichia* sp may be conducted in a medium and under culture conditions that are suitable for the corresponding microorganism. The medium and culture conditions suitable for the corresponding microorganism can be readily selected and adjusted by any person skilled in the art to which it pertains. Examples of the culturing method include batch type, continuous type and fed-batch type manners, but are not limited thereto.

In a specific embodiment of the present invention, the step of culturing the microorganism belonging to the genus *Escherichia* sp. may be conducted by culturing the strain in a typical medium that is supplemented with appropriate carbon sources including sucrose, nitrogen sources, amino acids, and vitamins under aerobic conditions and temperature or pH control.

The medium used in the present invention includes sucrose or molasses containing a high concentration of sucrose as a main carbon source, and may include various carbon sources in addition to the main carbon source. The nitrogen source included in the medium may be used either singly or in combinations of organic nitrogen sources such as peptone, yeast extract, broth, malt extract, corn steep liquor, and soy bean, and inorganic nitrogen sources such as urea, ammonium sulfate, ammonium chloride, ammonium phosphate, ammonium carbonate and ammonium nitrate. In the medium, phosphorus sources such as potassium dihydrogen phosphate, dipotassium hydrogen phosphate or corresponding sodium-containing salts may be included. In addition, the medium may be supplemented with amino acids, vitamins, and appropriate precursors. These main components may be added to the media in a batch type or a continuous type.

During cultivation, compounds such as ammonium hydroxide, potassium hydroxide, ammonia, phosphoric acid, and sulfuric acid may be properly added so as to adjust the pH of the cultures. During cultivation, defoaming agents such as fatty acid polyglycol ester may be used so as to prevent the formation of foams. Generally, the cultivation temperature may be maintained at 27° C. to 37° C., and preferably at 30° C. to 35° C. The cultivation may be continued as long as a production amount of the desired material, L-amino acid is increased under the given conditions, and for example, for 10 to 100 hrs.

The method for producing an L-amino acid according to the present invention includes the step of recovering the L-amino acid from the culture of the microorganism. The method of recovering the L-amino acid from the culture may be performed by a proper method known in the art, depending on the culturing procedures, for example, batch type, continuous type or fed-batch type.

Hereinafter, the present invention will be described in more detail with reference to Examples. However, these Examples are for illustrative purposes only, and the invention is not intended to be limited by these Examples.

EXAMPLE 1

Cloning and Identification of Sequence of Scr Regulon which is Involved in Sucrose Assimilation (1) Cloning of Sucrose Assimilative Microorganism-Derived Scr Regulon To impart a sucrose assimilability to a sucrose non-assimilative *Escherichia* sp. microorganism, the gene cluster involved in sucrose assimilation, scr regulon was obtained from a sucrose assimilative microorganism. The scr regulon is composed of five genes, scrK (fructokinase), scrY (sucrose porin), scrA (sucrose-specific EIIBC component), scrB (sucrose-6-phosphate hydrolase), and scrR (LacI-related sucrose-specific repressor), and two operons, scrK and scrYAB are negatively controlled by the ScrR repressor (Mol, Microbiol. (1993) 9:195-209).

The Scr-PTS system, scrKYABR genes were obtained by PCR (Polymerase Chain Reaction) using each chromosome of *Klebsiella pneumoniae* (ATCC700721D-5) and *Erwinia carotobora* (ATCCBAA-672D) purchased from American Type Culture Collection as a template. The scrKYABR gene that is the scr regulon of *Klebsiella pneumoniae* was amplified by PCR using a pair of primers of SEQ ID NO. 1 and SEQ ID NO. 2, and the scrKYABR gene of *Erwinia carotobora* was amplified by PCR using a pair of primers of SEQ ID NO. 3 and SEQ ID NO. 4, so as to obtain five types of genes, which are consecutively present on each genome, as a single polynucleotide. The primers of SEQ ID NOs. 1 and 3 have the ApaLI restriction site, and the primers of SEQ ID NOs. 2 and 4 have the StuI restriction site. The primers used were prepared, based on information about scrKYABR and its surrounding sequence of *Klebsiella pneumoniae* (KEGG organism, kpn) and *Erwinia carotobora* (KEGG organism, eca) available in the KEGG (Kyoto Encyclopedia of Genes and Genomes).

PCR was performed under the conditions including denaturation at 94° C. for 3 min, 25 cycles of denaturation at 94° C. for 30 sec, annealing at 56° C. for 30 sec, and polymerization of at 72° C. for 5 min, and then polymerization for at 72° C. for 7 min. As a result, a polynucleotide of 7046 bp was obtained from *Klebsiella pneumoniae*, and a polynucleotide of 7223 bp was obtained from *Erwinia carotobora*. Each polynucleotide obtained by PCR was treated with ApaLI and FspI, and then cloned into the ApaLI and FspI sites of a pACYC177 vector. Thereafter, K. coli DH5α was transformed with the vector, and spread on a MacConkey agar plate containing 1% sucrose. Of colonies, deep purple colonies were selected, and then plasmids derived from *Klebsiella pneumoniae* and *Erwinia carotobora* were obtained using typical plasmid miniprep.

(2) Identification of Sequence of ScrKYABR Gene (2-1) *Klebsiella pneumoniae*-Derived Scr Regulon The plasmid containing the scr regulon of *Klebsiella pneumoniae* obtained in (1) was designated as pAscrKP, and the sequence (SEQ ID NO. 5) of scrKYABR cloned into the ApaLI and FspI sites was determined by a sequence determination method typically used in the art. FIG. 1 shows the construction of a recombinant plasmid pAscrKP containing *Klebsiella pneumoniae* (ATCC700721)-derived scrKYABR. In the scrKYABR sequence of SEQ ID NO. 5, the position from 307 to 1230 was determined as the scrK gene (SEQ ID NO. 6), the position from 1395 to 2912 was identified as the scrY gene (SEQ ID NO. 7), the position from 3017 to 4387 was identified as the scrA gene (SEQ ID NO. 8), the position from 4387 to 5787 was identified as the scrB gene (SEQ ID NO. 9), and the position from 5817 to 6821 was identified as the scrR gene (SEQ ID NO. 10), (2-2) *Erwinia carotobora*-Derived Scr Regulon The plasmid containing the scr regulon of *Erwinia carotobora* obtained in (1) was designated as pAscrEC, and the DNA sequence (SEQ ID NO. 11) of scrKYABR cloned into the ApaLI and FspI sites was determined by a sequence determination method typically used in the art. In the scrKYABR sequence of SEQ ID NO. 11, the position from 412 to 1347 was identified as the scrK gene (SEQ ID NO. 12), the position from 1538 to 3073 was identified as the scrY gene (SEQ ID NO. 13), the position from 3153 to 4523 was identified as the scrA gene (SEQ ID NO. 14), the position from 4523 to 5932 was identified as the scrB gene (SEQ ID NO. 15), and the position from 5963 to 6982 was identified as the scrR gene (SEQ ID NO. 16).

EXAMPLE 2

Construction of Sucrose Assimilative, L-Amino Acid Producing Microorganism (1) Transformation with Recombinant Plasmid In order to examine whether a threonine-producing *E. coli* grows using sucrose and produces threonine efficiently, when the *E. coli* is transformed with each of the gene cluster involved in sucrose assimilation, scr regulon-containing pAscrKP (SEQ ID NO. 17) and pAscrEC (SEQ ID NO. 18) obtained in Example 1, each of the plasmids was introduced into coli ABA5G by a typical transformation method. The *E. coli* ABA5G transformed with pAscrKP or pAscrEC was spread on a MacConkey agar plate containing 1% sucrose. Of colonies, deep purple colonies were selected. PCR was performed to confirm that the selected colonies had the sucrose assimilation related gene-containing plasmid.

(2) Production of Threonine by a Microorganism Transformed with pAscrKP or pAscrEA The colony obtained in (1) was cultured on a LB solid medium (1 g of tryptone, 1 g of NaCl, 0.5 g/100 ml of yeast extract, 1.5% agar) in a 33° C. incubator overnight. One loop of the cultured strain was inoculated in 25 mL of a titration medium having the composition of the following Table 1 and sucrose as a main carbon source, and then cultured in a 33° C. incubator at 200 rpm for 70 hrs.

TABLE 1

| Composition | Concentration (per liter) |
|---|---|
| Sucrose | 70 g |
| $KH_2PO_4$ | 2 g |
| $(NH_4)_2SO_4$ | 25 g |
| $MgSO_4 \cdot 7H_2O$ | 1 g |
| $FeSO_4 \cdot 7H_2O$ | 5 mg |
| $MnSO_4 \cdot 4H_2O$ | 5 mg |
| Yeast extract | 2 g |
| Calcium carbonate | 30 g |
| pH | 6.8 |

As a control group, the parental strain *E. coli* ABA5G transformed with no plasmid was used, and cultured in the medium having the composition of Table 1 using glucose instead of sucrose, in order to compare sucrose utilization rate to glucose utilization rate and threonine productivity. The results are summarized in the following Table 2.

TABLE 2

|  | Glucose (70 g/L) | | Sucrose (70 g/L) | |
| --- | --- | --- | --- | --- |
|  | OD | L-threonine (g/L) | OD | L-threonine (g/L) |
| ABA5G | 14.7 | 21.5 | — | — |
| ABA5G/pAscrEC | 14.4 | 21.6 | 8.4 | 12.2 |
| ABA5G/pAscrKP | 14.6 | 21.2 | 15.0 | 26.5 |

As shown in Table 2, the pAscrEC-harboring *E. coli* ABA5G/pAscrEC utilized 44.3 g/L of sucrose (data not shown) and produced 12.2 g/L of L-threonine, and the pAscrKP-harboring *E. coli* ABA5G/pAscrKP utilized 70 g/L of sucrose which is all of the sucrose contained in the culture medium, and produced 26.5 g/L of L-threonine during 70 hr cultivation. It was found that the pAscrEC or pAscrKP-harboring *E. coli* ABA5G utilized sucrose, while the parental strain *E. coli* ABA5G transformed with no plasmid did not utilize sucrose. In addition, the pAscrKP-harboring ABA5G was found to show more excellent sucrose utilization and threonine productivity than the pAscrEC-harboring ABA5G.

In particular, the pAscrKP-harboring ABA5G produced 21.2 g/L of L-threonine in the titration medium containing glucose, but 26.5 g/L of L-threonine in the titration medium containing sucrose, indicating a 1.3 times increase in the L-threonine productivity.

Therefore, the pAscrKP-harboring recombinant strain showed excellent sucrose utilization and L-threonine productivity, and thus the transformed microorganism was designated as CA03-0207, deposited in the international depository authority, Korean Culture Center of Microorganism, which is the Subsidiary Culture Collection of the Korean Federation of Culture Collections, (located at 361-221, Hongje-1-dong, Seodaemon-gu, Seoul, Korea) on Feb. 23, 2009, and assigned accession number KCCM 10993, It will be apparent to those skilled in the art that various modifications and changes may be made thereto without departing from the scope and spirit of the invention. Therefore, it should be understood that the above embodiments are not limitative, but illustrative in all aspects.

The sequences of SEQ ID NOs. 1 to 21 described herein are listed in the accompanying sequence listing.

EFFECT OF THE INVENTION

The microorganism having a sucrose assimilability and an L-amino acid producing ability according to the present invention is used to economically produce an L-amino acid using inexpensive sucrose as a carbon source.

What is claimed:

1. An isolated microorganism belonging to the genus *Escherichia*, wherein the microorganism comprises *Klebsiella pneumoniae*-derived genes encoding fructokinase, sucrose porin, sucrose PTS permease, sucrose hydrolase, and sucrose transcriptional regulator and a sucrose PTS (phosphoenolpyruvate dependent sucrose phosphotransferase system) comprising Enzyme I (EI), histidine protein, and glucose-specific enzyme IIA (EIIAcrr$^{Glc}$).

2. The isolated microorganism according to claim 1, wherein the genes encoding fructokinase, sucrose porin, sucrose PTS permease, sucrose hydrolase, and sucrose transcriptional regulator are scrK of SEQ ID NO. 6, scrY of SEQ ID NO. 7, scrA of SEQ ID NO. 8, scrB of SEQ ID NO. 9, and scrR of SEQ ID NO. 10, respectively.

3. The isolated microorganism according to claim 1, wherein the microorganism is obtained by transforming a sucrose non-assimilative microorganism belonging to the genus *Escherichia* with a recombinant vector comprising the sequence of SEQ ID NO. 17.

4. The isolated microorganism according to claim 1, wherein the microorganism is *E. coli*.

5. The isolated microorganism according to claim 4, wherein the *E. coli* is *E. coli* CA03-0207 (KCCM 10993).

6. The isolated microorganism according to claim 1, wherein the L-amino acid is L-threonine.

7. A method for producing an L-amino acid, comprising culturing an isolated microorganism belonging to the genus *Escherichia* in a medium containing sucrose as a carbon source; and recovering an L-amino acid from the culture medium,
   wherein the microorganism has sucrose assimilability and the ability to produce L-amino acids and comprises sucrose metabolic genes from *Klebsiella pnmeumoniae* encoding fructokinase, sucrose porin, sucrose PTS permease, sucrose hydrolase, and sucrose transcriptional regulator, and
   wherein the microorganism comprises sucrose PTS (phosphoenolpyruvate dependent sucrose phosphotransferase system) activity comprising enzyme I (EI), histidine protein, and glucose-specific enzyme IIA (EIIAcrr$^{Glc}$).

8. The method according to claim 7, wherein the L-amino acid is L-threonine.

9. The method according to claim 7, wherein the genes encoding fructokinase, sucrose porin, sucrose PTS permease, sucrose hydrolase, and sucrose transcriptional regulator are scrK of SEQ ID NO. 6, scrY of SEQ ID NO. 7, scrA of SEQ ID NO. 8, scrB of SEQ ID NO. 9, and scrR of SEQ ID NO. 10, respectively.

10. The method according to claim 7, wherein the isolated microorganism is obtained by transforming a microorganism with a recombinant vector comprising the sequence of SEQ ID NO. 17.

11. The method according to claim 7, wherein the isolated microorganism is *E. coli*.

12. The method according to claim 11, wherein the *E. coli* is *E. coli* CA03-0207 (KCCM 10993).

\* \* \* \* \*

UNITED STATES PATENT AND TRADEMARK OFFICE
CERTIFICATE OF CORRECTION

PATENT NO. : 8,623,620 B2  
APPLICATION NO. : 13/254072  
DATED : January 7, 2014  
INVENTOR(S) : Ju et al.

Page 1 of 1

It is certified that error appears in the above-identified patent and that said Letters Patent is hereby corrected as shown below:

On the Title Page, item (73), Assignee, please change "CJ Chieljedang Corporation" to --CJ Cheiljedang Corporation--.

In the Claims:

In column 59, claim 1, line 3, after "microorganism comprises" insert --sucrose metabolic genes from--.

In column 59, claim 1, line 4, delete the words "*pnuemoniae*-derived genes" and replace them with --*pneumoniae*--.

In column 59, claim 2, line 13, delete "scrK" and insert --*scrK*--; delete "scrY" and insert --*scrY*--.

In column 59, claim 2, line 14, delete "scrA" and insert --*scrA*--; delete "scrB" and insert --*scrB*--.

In column 59, claim 2, line 15, delete "scrR" and insert --*scrR*--.

In column 60, claim 9, line 18, delete "scrK" and insert --*scrK*--; delete "scrY" and insert --*scrY*--; delete "scrA" and insert --*scrA*--.

In column 60, claim 9, line 19, delete "scrB" and insert --*scrB*--; delete "scrR" and insert --*scrR*--.

Signed and Sealed this  
Thirteenth Day of May, 2014

Michelle K. Lee  
*Deputy Director of the United States Patent and Trademark Office*